(12) United States Patent
Matsunaga et al.

(10) Patent No.: US 9,464,371 B2
(45) Date of Patent: Oct. 11, 2016

(54) FIBER STACKING DEVICE

(71) Applicant: KAO CORPORATION, Tokyo (JP)

(72) Inventors: Ryuji Matsunaga, Utsunomiya (JP);
Hiroshi Maruyama, Utsunomiya (JP);
Tomoyuki Motegi, Haga-gun (JP)

(73) Assignee: KAO CORPORATION, Tokyo (JP)

( * ) Notice: Subject to any disclaimer, the term of this patent is extended or adjusted under 35 U.S.C. 154(b) by 162 days.

(21) Appl. No.: 14/352,952

(22) PCT Filed: Oct. 12, 2012

(86) PCT No.: PCT/JP2012/076505
§ 371 (c)(1),
(2) Date: Apr. 18, 2014

(87) PCT Pub. No.: WO2013/058195
PCT Pub. Date: Apr. 25, 2013

(65) Prior Publication Data
US 2014/0305570 A1 Oct. 16, 2014

(30) Foreign Application Priority Data

Oct. 19, 2011 (JP) ................................. 2011-229421

(51) Int. Cl.
*A61F 13/15* (2006.01)
*D04H 1/732* (2012.01)
(Continued)

(52) U.S. Cl.
CPC ........... *D04H 1/44* (2013.01); *A61F 13/15577* (2013.01); *A61F 13/15617* (2013.01);
(Continued)

(58) Field of Classification Search
CPC .................. A61F 13/15577; A61F 13/15617;
A61F 13/15626; A61F 13/15634; A61F 13/15658; A61F 2013/15821; A61F 2013/15926; A61F 2013/15934; A61F 2013/15943; A61F 2013/15991; D04H 1/732; D04H 1/736
See application file for complete search history.

(56) References Cited

U.S. PATENT DOCUMENTS 4,666,647 A   5/1987   Enloe et al.
4,761,258 A   8/1988   Enloe
(Continued)

FOREIGN PATENT DOCUMENTS

CN   101277663 A   10/2008
EP   0 226 939 A2   7/1987
(Continued)

OTHER PUBLICATIONS

Extended European Search Report, issued May 11, 2015, for European Application No. 12840910.9.
(Continued)

*Primary Examiner* — Michael Tolin
(74) *Attorney, Agent, or Firm* — Birch, Stewart, Kolasch & Birch, LLP

(57) ABSTRACT

A rotating drum (1) has a collecting/stacking recess (2) in the outer peripheral surface thereof, and includes: a drum body (3); and an air-permeable porous member (4) that forms the bottom surface (2A) of the collecting/stacking recess (2). The porous member (4) is sandwiched between: an outer shaping member (6) arranged so as to oppose the bottom surface (2A); and an inner shaping member (7) arranged between the porous member (4) and the drum body (3). Both the shaping members (6, 7) are arranged so as to overlap the porous member (4). Each shaping member (6, 7) has a recess-bottom-surface corresponding section (6A, 7A) that overlaps the bottom surface (2A) of the collecting/stacking recess (2) in a planar view thereof, and that is constituted by: a plurality of openings (65, 75) that penetrate the recess-bottom-surface corresponding section (6A, 7A) in the thickness direction; and an opening defining section (60, 70) that partitions and forms the openings (65, 75). The opening defining section (70) of the inner shaping member (7) corresponds to the opening defining section (60) of the outer shaping member (6).

13 Claims, 8 Drawing Sheets

(51) Int. Cl.
   *D04H 1/736* (2012.01)
   *D04H 1/44* (2006.01)
(52) U.S. Cl.
   CPC ... *A61F13/15626* (2013.01); *A61F 13/15658* (2013.01); *D04H 1/732* (2013.01); *D04H 1/736* (2013.01); *A61F 2013/15926* (2013.01); *A61F 2013/15943* (2013.01); *A61F 2013/15991* (2013.01)

(56) References Cited

U.S. PATENT DOCUMENTS

| | | | |
|---|---|---|---|
| 5,004,579 A * | 4/1991 | Wislinski | A61F 13/15577 264/112 |
| 6,330,735 B1 | 12/2001 | Hahn et al. | |
| 7,704,441 B2 * | 4/2010 | Van Valkenburgh | A61F 13/15626 264/113 |
| 2006/0105075 A1 | 5/2006 | Otsubo | |
| 2009/0281511 A1 | 11/2009 | Fukae | |
| 2012/0270715 A1 | 10/2012 | Motegi et al. | |
| 2013/0059713 A1 | 3/2013 | Nakano | |
| 2013/0139960 A1 | 6/2013 | Maruyama et al. | |

FOREIGN PATENT DOCUMENTS

| | | |
|---|---|---|
| EP | 2 859 868 A1 | 4/2015 |
| JP | 62-206071 A | 9/1987 |
| JP | 2004-530799 A | 10/2004 |
| JP | 2006-141615 A | 6/2006 |
| JP | 4499792 B2 | 7/2010 |
| JP | 2011-200568 A | 10/2011 |
| JP | 2012-16584 A | 1/2012 |
| JP | 2013-85856 A | 5/2013 |
| WO | WO 02/066723 A1 | 8/2002 |
| WO | WO 2007/037357 A1 | 4/2007 |
| WO | WO 2011/068062 A1 | 6/2011 |
| WO | WO 2011/118495 A1 | 9/2011 |

OTHER PUBLICATIONS

International Preliminary Report on Patentability and English translation of the Written Opinion of the International Searching Authority, dated May 1, 2014, for International Application No. PCT/JP2012/076505.

International Search Report Issued in PCT/JP2012/076505, mailed on Nov. 20, 2012.

* cited by examiner

US 9,464,371 B2

FIBER STACKING DEVICE

TECHNICAL FIELD

The present invention relates to a fiber stacking device that includes a rotating drum having a collecting/stacking recess in the outer peripheral surface thereof, and that is used for obtaining shaped products (absorbent cores) having predetermined shapes by stacking shaped-product materials—e.g. fiber materials, such as pulp, and water-absorbent polymers—in the collecting/stacking recess.

BACKGROUND ART

A known example of a device for manufacturing absorbent cores used for sanitary products (absorbent articles), such as disposable diapers and sanitary napkins, is a fiber stacking device that includes a rotating drum having a collecting/stacking recess in the outer peripheral surface thereof, wherein: a shaped-product material, such as pulp, is supplied to the outer peripheral surface of the rotating drum in a dispersed, airborne state while rotating the rotating drum; the shaped-product material is stacked in the collecting/stacking recess by suction from the bottom surface of the collecting/stacking recess; and the fiber stack in the collecting/stacking recess is released from the collecting/stacking recess by suction from a suction means arranged in opposition to the collecting/stacking recess, and is transferred onto the suction means.

As an example of a rotating drum for the aforementioned fiber stacking device, Patent Literature 1 discloses a rotating drum including a porous air-permeable member, such as a wire mesh, that forms the bottom surface of a collecting/stacking recess, and masking members attached onto the air-permeable member so as to be movable in a predetermined direction, whereby an absorbent core having a desired shape and basis weight distribution can be manufactured by moving the masking members.

Patent Literature 2 discloses a rotating chum including an air-permeable porous plate that has a multitude of suction pores and that forms the bottom surface of a collecting stacking recess, and a honeycomb structure rectifier that is for rectifying the flow of air and that is arranged integrally to the porous plate on the inside thereof. According to Patent Literature 2, the use of such a rotating drum stabilizes the profile of the absorbent core and reduces unevenness in weight of the absorbent core.

Patent Literature 3 discloses a rotating drum wherein a plurality of protrusions, each protruding outward in the drum's radial direction and elongated in the drum's circumferential direction, are formed over the entire area of an air-permeable bottom surface of a collecting/stacking recess. The protrusions are arranged continuously or intermittently in the circumferential direction, and arranged so as to be separated from one another by a predetermined distance in the axial direction of the drum. According to Patent Literature 3, by using such a rotating drum, shaped-product materials are stacked in the recessed spaces other than the protrusions, and thus, the final shaped product (absorbent core) has a plurality of intermittently arranged low-rigidity sections formed by the protrusions, and is thus provided with uniform rigidity and excellent flexibility and is capable of efficiently absorbing body fluid with the entire area thereof.

Patent Literature 4 discloses a rotating drum wherein a spacing member having a plurality of openings, and a gas flaw rate regulating layer having a plurality of openings, are layered in this order on the inner side of a web layer that forms the bottom surface of a collecting/stacking recess (i.e., on the side where shaped-product materials are not stacked). According to Patent Literature 4, the bottom surface (i.e., the web layer) of the collecting/stacking recess is not flat, but the bottom surface has recesses in the central section in the drum's width direction, and thus, sections in the shaped product that correspond to the recesses can be made into high basis-weight sections in which the amount of shaped-product materials stacked is greater compared to other sections.

CITATION LIST

Patent Literature

Patent Literature 1: U.S. Pat. No. 6,330,735 B1
Patent Literature 2: US 2009281511 A1
Patent Literature 3: US 2006105075 A1
Patent Literature 4: EP 0226939 A2

SUMMARY OF INVENTION

Technical Problem

In the fiber stacking devices configured as above, a fiber stack obtained by stacking shaped-product materials in the collecting/stacking recess of the rotating drum is released from the collecting/stacking recess by suction from a suction means arranged in opposition to the collecting/stacking recess and is transferred onto the suction means. At the time of releasing/transferring, there are cases where the fiber stack gets caught in a gap etc. formed between constituent members in the collecting/stacking recess, and cannot be released smoothly from the collecting/stacking recess, possibly causing faulty transferring of the fiber stack. Faulty fiber-stack transferring not only decreases manufacturing efficiency, but may also give rise to problems—such as loss of shape of the fiber stack and misalignment in transferring position—that lead to degradation in quality of the shaped product, which is the final product. Thus, it is desired to prevent the occurrence of such problems.

Solution to Problem

The present invention provides a fiber stacking device including a rotating drum that has a collecting/stacking recess in an outer peripheral surface thereof, wherein the rotating drum forms a shaped product by stacking a shaped-product material by sucking the material with a bottom surface of the collecting/staking recess, wherein: the rotating drum includes a drum body, and an air-permeable porous member that forms the bottom surface of the collecting/stacking recess; the porous member is sandwiched between an outer shaping member arranged so as to oppose the bottom surface of the collecting/stacking recess, and an inner shaping member arranged between the porous member and the drum body; both of the shaping members are arranged so as to overlap the porous member; each of the shaping members has a recess-bottom-surface corresponding section that overlaps the bottom surface of the collecting/stacking recess in a planar view of the collecting/stacking recess; each recess-bottom-surface corresponding section is constituted by a plurality of openings that penetrate the recess-bottom-surface corresponding, section in the thickness direction, and an opening defining section that partitions and forms the openings; and the opening defining section of the inner shaping member corresponds to the opening defining section of the outer shaping member.

The present invention also provides a method for manufacturing an absorbent core by using the aforementioned fiber stacking device, the absorbent core manufacturing method involving: a fiber stacking, step of sucking and stacking, in the collecting/stacking recess of the rotating drum, an absorbent-core material supplied on an air stream.

The present invention also provides a method for manufacturing an absorbent article that includes an absorbent core and a sheet material to which the absorbent core is fixed, the absorbent article manufacturing method involving; a step of fixing, onto the sheet material, the absorbent core obtained by executing the aforementioned manufacturing method.

Advantageous Effects of Invention

With the fiber stacking device of the present invention, fiber stacks in the collecting stacking recess of the rotating drum can be released smoothly, and faulty transferring is less prone to occur, and thus, shaped products with a desired shape can be manufactured efficiently. Further, with the absorbent core manufacturing method of the present invention, it is possible to efficiently manufacture high-quality absorbent cores with no loss of shape, etc.

DESCRIPTION OF EMBODIMENTS

The present invention relates to a fiber stacking device in which fiber stacks in a collecting/stacking recess of a rotating drum can be released smoothly and faulty transferring is less prone to occur, and thus, shaped products with a desired shape can be manufactured efficiently.

Figure 1:
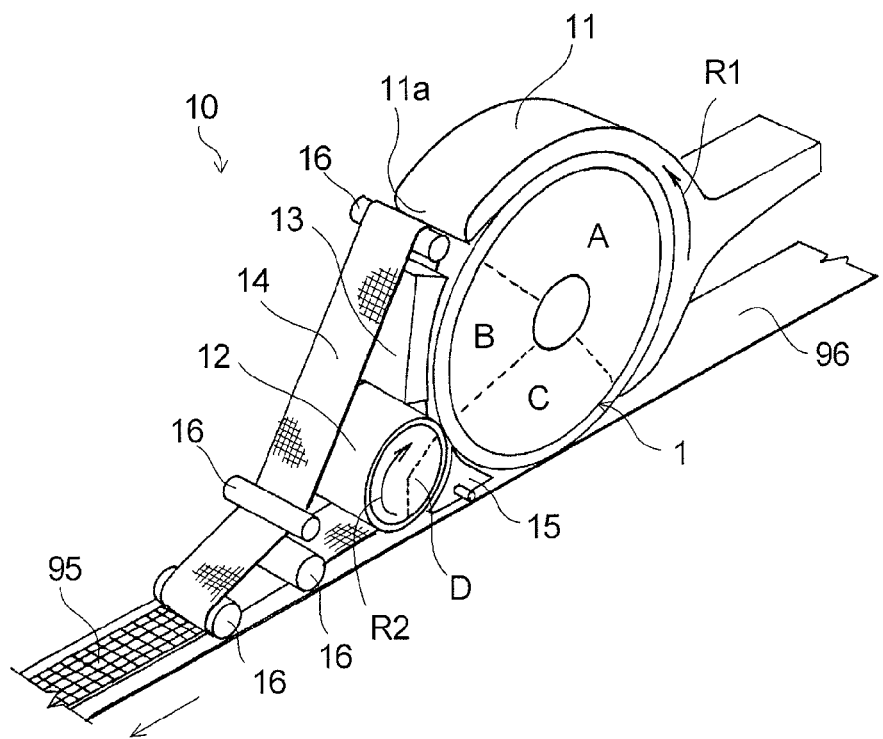
FIG. 1 is a schematic perspective view of an embodiment of a fiber stacking device of the present invention.
Figure 2:
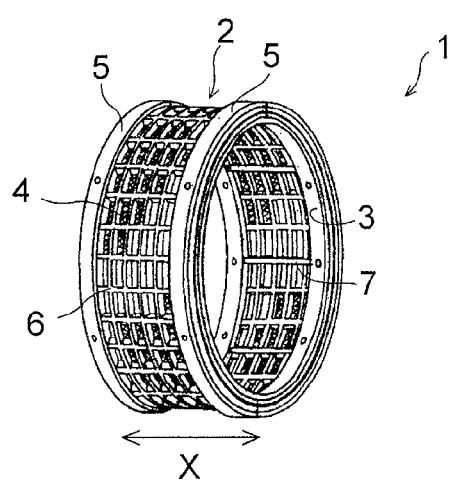
FIG. 2 is a perspective view illustrating a rotating drum of the fiber stacking device illustrated in FIG. 1.
Figure 3:
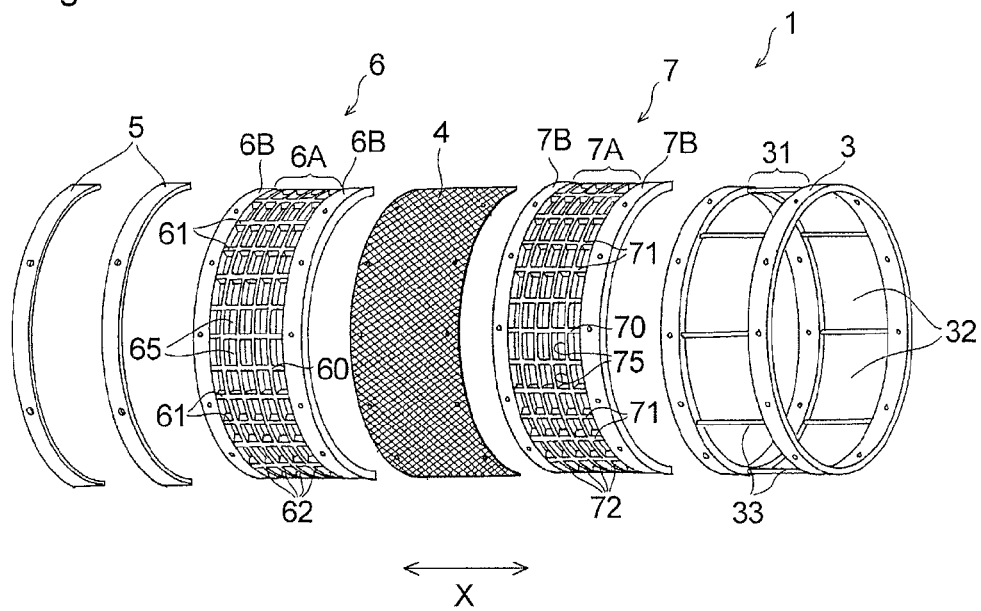
FIG. 3 is to diagram explaining the construction of the rotating drum illustrate FIG. 2.
Figure 4:
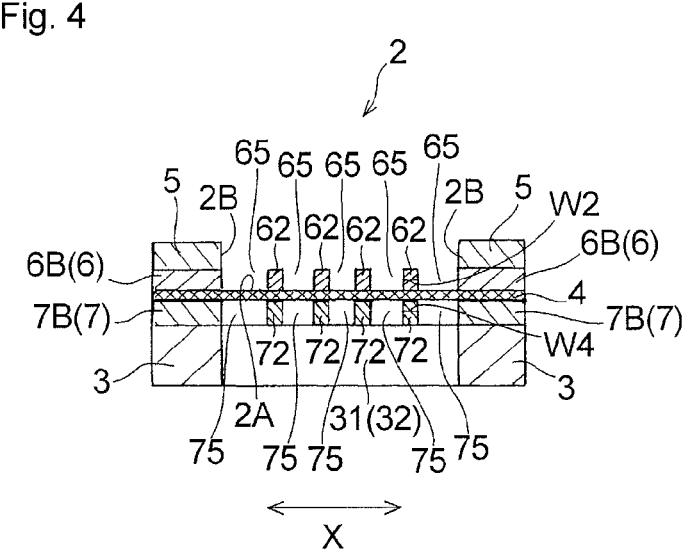
FIG. 4 is a cross-sectional view illustrating a cross section of the outer peripheral surface, and its vicinity, of the rotating drum illustrated in FIG. 2, taken along the width direction of the drum.

The fiber stacking device of the present invention will be described below according to a preferred embodiment thereof with reference to the drawings. FIG. 1 illustrates a fiber stacking device 10 which is an embodiment of the fiber stacking device of the present invention. FIGS. 2 to 4 illustrate a rotating, drum 1 provided to the fiber stacking device 10. The fiber stacking device 10 includes a rotating drum 1 that has a collecting/stacking recess 2 in the outer peripheral surface thereof, wherein the rotating drum 1 forms a shaped product by stacking a shaped-product material by sucking the material with the bottom surface 2A of the collecting/stacking recess 2.

As illustrated in FIG. 1, the fiber stacking device 10 includes: the aforementioned rotating drum 1 driven to rotate in the direction of arrow R1; a duct 11 that supplies shaped-product materials to the other peripheral surface of the rotating drum 1; a transfer roller 12 that is driven to rotate in the direction of arrow R2, and that is arranged obliquely below the rotating drum 1; and a vacuum conveyor (not illustrated) arranged below the transfer roller 12. The vacuum conveyor of the fiber stacking device 10 is constructed like an ordinary vacuum conveyor employed in this type of fiber stacking device, and includes: an endless, air-permeable belt that is spanned between a drive roller and a driven roller; and a vacuum box arranged at a position opposing the transfer roller 12 across the air-permeable belt.

Further, in the fiber stacking device 10: a vacuum box 13 is provided between the duct 11 and the transfer roller 12 in the circumferential direction of the rotating drum 1; a mesh belt 14 is arranged so as to pass between the vacuum box 13 and the rotating drum 1 and between the transfer roller 12 and the rotating drum 1; and windshield plates 15 are provided close to the outer peripheral surface of the transfer roller 12.

Below, the relating drum 1, which is the main characteristic part of the fiber stacking device 10, will be described. As illustrated in FIGS. 2 to 4, the rotating drum of the present embodiment has, in its outer peripheral surface, a collecting/stacking recess 2 in which shaped-product materials are stacked, and includes: a drum body 3; and an air-permeable porous member 4 that forms the bottom surface 2A of the collecting/stacking recess 2 and in which a multitude of air-permeation holes are formed. The collecting/stacking recess 2 is formed continuously in the outer peripheral surface or the rotating drum 1 along the entire length in the circumferential direction. The porous member 4 has a flat form; thus, the bottom surface 2A of the collecting/stacking recess 2 formed by the porous member 4 has a flat form, and substantially has no projections and recesses. Stated differently, the sections of the bottom surface 2A that correspond to openings 65 (i.e., spaces surrounded by linear members 61, 62) in a later-described outer shaping member 6 (recess-bottom-surface corresponding section 6A) (i.e., sections that overlap the aforementioned corresponding sections in a planar view of the collecting/stacking recess 2) are flat. It should be noted that, herein, "projections and recesses" refer to projections and recesses which affect the amount of shaped-product materials stacked (i.e., projections and recesses which are intentionally formed in order to partially differentiate the stacking amount), and do not include fine projections and recesses which do not affect the amount of shaped-product materials stacked.

The drum body 3 is made of a stiff, metal tube, and has, in the central section in the drum's width direction (i.e., the direction of the rotation axis of the rotating drum; the direction indicated by symbol X in the figure), a recess-bottom-surface corresponding section 31 that overlaps the bottom surface 2A of the collecting/stacking recess 2 in a planar view thereof. Herein, "planar view" refers to a view in which an object (collecting/stacking recess, etc.) is viewed from the outside along the direction of the normal to the outer peripheral surface of the rotating drum 1 (i.e., along a direction orthogonal to the rotation direction the rotating drum 1). The recess-bottom-surface corresponding section 31 of the drum body 3 is constituted by a plurality of through openings 32 (eight in the embodiment illustrated in FIG. 3) that penetrate the recess-bottom-surface corresponding section 31 in the thickness direction, and air-impermeable ribs 33 each located between two adjacent through openings 32, 32. By being provided with the through openings 32, the recess-bottom-surface corresponding section 31, as a whole, is air-permeable. The plurality of through openings 32 are formed along the circumferential direction of the drum body 3 at predetermined intervals. Between two through openings 32, 32 adjacent to one another in the circumferential direction, an air-impermeable rib 33 is funned so as to extend in the drum's width direction X. The ribs 33 mainly serve to improve the strength of the drum body 3 itself and to improve the strength of the bottom section of the collecting/stacking recess 2.

The porous member 4 conveys vacuum air, which is generated from inside the drum, to the outside of the drum, and holds shaped-product materials, such as pulp, that are carried on the vacuum air. The porous member 4 itself (i.e., the member that defines the air-permeation holes) is made of an air-impermeable or sparingly air-permeable material, but a multitude of fine air-permeation holes are formed over the entire area of the porous member 4, so thus, the air-permeation holes function as suction holes for sucking the shaped-product materials while the collecting/stacking recess 2 passes over a space, in the rotating drum 1, that is maintained at negative pressure. The porous member 4 may have, as the air-permeation holes, e.g. circular holes with a diameter of about 0.2 to 0.6 mm formed at a pitch or about 0.4 to 1.5 rum in a staggered pattern. Examples of air-impermeable materials include stainless steel, iron, aluminum, and polymer materials. An example of a sparingly air-permeable material includes material in which micro-holes are made in a member made of an air-impermeable material. As the porous member 4, it is possible to use a metal or resin mesh, or a porous metal plate or resin plate in which a multitude of fine holes are formed in a metal or resin plate by etching or punching. As an example of a porous metal plate or resin plate for forming the porous member 4, it is possible to use a plate in which a multitude of fine holes are formed, for example, by punching or etching in a metal or resin plate (e.g. stainless steel plate) with a thickness of about 0.1 to 0.5 mm. As described above, in the present embodiment, the bottom surface 2A of the collecting/stacking recess 2 has a flat form; so, the porous member 4 that forms the flat-form bottom surface 2A substantially has no projections and recesses, and thus, the apparent thickness of the porous member 4 is uniform over the entire area in the circumferential direction of the rotating drum 1.

As illustrated in FIGS. 2 to 4, the rotating drum 1 of the present embodiment also includes ring members 5 that form the respective inner-side surfaces 2B of the collecting/stacking recess 2, in addition to the drum body 3 and the porous member 4. The ring members 5 define the length of the collecting/stacking recess 2 in the drum's width direction X (i.e., the width of the collecting/stacking recess 2), and are arranged on the respective side sections, in the width direction, of the outer peripheral surface of the rotating drum 1 with the collecting/stacking recess 2 sandwiched between the ring members 5. The distance between the ring member 5 on the side of one widthwise side section and the ring member 5 on the side of the other side section (i.e. the distance between the pair of right and left ring members) constitutes the width of the collecting/stacking recess 2. Further, the inner end surface of the ring member 5 formed along the circumferential direction of the rotating drum 1 forms a portion of the inner-side surface 2B of the collecting/stacking recess 2, and is an element that determines the thickness of the collecting/stacking recess 2. The positions for attaching the respective ring members 5 (the distance between the pair of right and left ring members) and the thickness thereof (the height or the inner end surface) are determined with consideration given to, for example, the width of the shaped product (fiber stack) and the amount of shaped-product materials to be stacked. The ring member 5 is air-impermeable and is made, for example, of a metal plate such as a stainless steel plate, and its thickness is, for example, about 2 to 12 mm.

One of the main features of the rotating drum 1 of the present embodiment is that the porous member 4, which forms the bottom surface 2A of the collecting/stacking recess 2, is sandwiched between an outer shaping member 6 arranged so as to oppose the bottom surface 2A of the collecting/stacking recess 2, and an inner shaping member 7 arranged between the porous member 4 and the drum both 3, as illustrated in FIGS. 3 and 4. Both of the shaping members 6, 7 are arranged so as to overlap the porous member 4, as illustrated in FIGS. 3 and 4, and no other member is arranged between the outer shaping member 6 and the porous member 4, and between the inner shaping member 7 and the porous member 4. The length in the drum's width direction X (i.e., the width) of each of the outer shaping member 6 and the inner shaping member 7 is the same as that of the porous member 4, and each shaping member has, in the central section in the drum's width direction X, a recess-bottom-surface corresponding section 6A, 7A that overlaps the bottom surface 2A of the collecting/stacking recess 2 in a planar view thereof (cf. FIG. 3). Here, "planar view" has the aforementioned meaning.

As illustrated in FIGS. 3 and 4, the recess-bottom-surface corresponding sections 6A, 7A of the respective shaping members 6, 7, which overlap the bottom surface 2A of the collecting/stacking recess 2 in a planar view of the collecting/stacking recess 2, are each constituted by a plurality of openings 65, 75 that penetrate the recess-bottom-surface corresponding section 6A, 7A in the thickness direction, and an opening defining section 60, 70 that partitions and forms the openings 65, 75.

In the present embodiment, as illustrated in FIGS. 3 and 4, the opening defining sections 60, 70 of the respective shaping members 6, 7 are each constituted by linear members 61, 62, 71, 72 extending along the bottom surface 2A of the collecting/stacking recess 2 (i.e., along the outer peripheral surface of the rotating drum 1). Herein, "extend along the bottom surf 2A of the collecting/stacking recess 2" refers both to cases where the opening defining sections 60, 70 (the linear members 61, 62, 71, 72) are in contact with the bottom surface 2A (the porous member 4) and cases where they are not in contact with the bottom surface 2A.

More specifically, as illustrated in FIG. 3, the opening defining section 60 of the outer shaping member 6 includes a plurality of width-wise linear members 61 that, in a planar view, are each in a straight line extending in the drum's width direction X, and a plurality of circumference-wise linear members 62 (four in the present embodiment) that, in a planar view, are each in a straight line orthogonal to the plurality of width wise linear members 61. The opening defining section 60 of the outer shaping member 6 is formed in a lattice pattern, in planar view, by the linear members 61, 62. The openings 65 in the outer shaping member 6 are located at the respective cells of the lattice and each have a rectangular shape in planar view.

Further, as illustrated in FIG. 3, the opening defining section 70 of the inner shaping member 7 includes a plurality of width-wise linear members 71 that, in a planar view, are each in a straight line extending in the drum's width direction X, and a plurality of circumference-wise linear members 72 (four in the present embodiment) that, in a planar view, are each in a straight line orthogonal to the plurality of width-wise linear members 71. The opening defining section 70 of the inner shaping member 7 is formed in a lattice pattern, in planar view, by the linear members 71, 72. The openings 75 in the inner shaping member 7 are located at the respective cells of the lattice and each have a rectangular shape in planar view.

The collecting/stacking recess 2 is partition ad by the opening defining section 60 of the outer shaping member 6 into a plurality of recesses that correspond to the plurality of openings 65 of the outer shaping member 6. Each recess is constituted by the porous member 4 (the bottom surface 2A), and side walls that consist of the opening defining section 60 and that are formed upright from the porous member 4 in the direction of the normal; and the entire porous member 4 forms a suction section that sucks shaped-product materials. The space in each recess surrounded by the side walls consisting of the opening defining section 60 (i.e., the inner space of each recess) is the opening 65.

The opening defining sections 60, 70 (the linear members 61, 62, 71, 72) of the respective shaping members 6, 7 are made of an air-impermeable or sparingly air-permeable material, like the porous member 4, and are air-impermeable. Herein, "air impermeability" of the opening defining sections 60, 70 refers to a property that makes vacuum air, which is generated from inside the drum, hard to permeate through the members (the opening defining sections 60, 70), and encompasses cases where vacuum air is completely prevented from permeating therethrough (i.e., cases where there is no air permeability) and also cases where the member as some air permeability, albeit low, but cannot adsorb shaped-product materials (pulp, etc.), which are in a dispersed airborne state outside the drum, by the vacuum air that permeates through the member (i.e., cases where there is substantially no air permeability). Unless otherwise stated, the aforementioned explanation applies to the description "air impermeability (air-impermeable)" in the present Description; for example, the air impermeability of the porous member 4 itself (i.e., the member that defines the air-permeation holes) has the same meaning as the air impermeability of the opening defining sections 60, 70. As described above, the opening defining sections 60, 70 (the linear members 61, 62, 71, 72) of the recess-bottom-surface corresponding sections 6A, 7A of the respective shaping members 6, 7 are air-impermeable, but because of the plurality of openings 65, 75 that allow the passage of air, the recess-bottom-surface corresponding sections, as a whole, have sufficient on permeability for sucking and stacking the shaped-product materials.

Whether to use an air-impermeable or sparingly air-permeable material as the material for forming the opening defining sections 60, 70 (the linear members 61, 62, 71, 72) may be chosen, as appropriate, depending on the use etc. of the shaped product (absorbent core) to be manufactured. Inventors found that, in cases where the air permeability of the opening defining sections 60, 70 is lower than the air permeability of the bottom surface 2A (the porous member 4) of the collecting/stacking recess 2, fiber stacking properties are improved and shaped-product materials can be stacked smoothly in the collecting stacking recess 2, and also, transferring properties are improved and the fiber stack in the collecting/stacking recess 2 can be transferred smoothly, compared to cases where the air permeability of the opening defining sections and that of the porous member are the same. Thus, it is preferable to select the material for forming the opening defining sections 60, 70 such that the air permeability of the defining sections 60, 70 becomes lower than that of the bottom surface 2A (the porous member 4) of the collecting/stacking recess 2.

In the present embodiment, the sections of the outer shaping member 6 other than the recess-bottom-surface corresponding section 6A—i.e., the side sections 6B, 6B of the outer shaping member 6 in the drum's width direction X—constitute ring-member corresponding sections that overlap the respective ring members 5 in a planar view of the outer peripheral surface of the rotating drum 1. The length in the drum's width direction X (i.e., the width) of each side section 6B of the outer shaping member 6 is the same as the width of each ring member 5. As illustrated in FIG. 4, as regards each side section 6B of the outer shaping member 6, the inner end surface thereof along the circumferential direction of the rotating drum 1 forms a surface that is flush with the inner end surface of the ring member 5, and forms the inner-side surface 2B of the collecting/stacking recess 2 together with the ring member 5. The side sections 6B of the outer shaping member 6 are made of an air-impermeable or sparingly air-permeable material like the recess-bottom-surface corresponding section 6A (the opening defining section 60), and is air-impermeable like the opening defining section 60.

Further, in the present embodiment, the sections at the inner shaping member 7 other than the recess-bottom-surface corresponding section 7A—i.e., the side sections 7B, 7B of the inner shaping member 7 in the drum's width direction X—constitute ring-member corresponding sections that overlap the respective ring members 5 in a planar view of the outer peripheral surface of the rotating drum 1. The length in the drum's width direction X (i.e., the width) of each side section 7B of the inner shaping member 7 is the same as the width of each ring member 5, and is thus the same as the width of the side section 6B of the outer shaping member 6. As illustrated in FIG. 3, as regards each side section 7B of the inner shaping member 7, the inner end surface thereof along the circumferential direction of the rotating drum 1 forms a surface that is flush with the inner end surface of the ring member 5 and the inner end surface of the side section 6B or the Outer shaping member 6. The side sections 7B of the inner shaping member 7 are made of an air-impermeable or sparingly air-permeable material like the recess-bottom-surface corresponding section 7A (the opening defining section 70), and is air-impermeable like the opening defining section 70.

The thickness of the recess-bottom-surface corresponding section 6A of the outer shaping member 6 is preferably 1 mm or greater and more preferably 2 mm or greater, and preferably 30 mm or less and more preferably 15 mm or less. More specifically, the thickness of the recess-bottom-surface corresponding section 6A is preferably from 1 to 30 mm and more preferably from 2 to 15 mm. The thickness of the side sections 6B may be set to be similar to the thickness of the recess-bottom-surface corresponding section 6A. The thickness of the recess-bottom-surface corresponding section 7A of the inner shaping member 7 is preferably 1 mm or greater and more preferably 2 mm or greater, and preferably 30 mm or less and more preferably 15 mm or less. More specifically, the thickness of the recess-bottom-surface corresponding section 7A is preferably from 1 to 30 mm and more preferably from 2 to 20 mm. The thickness of the side sections 7B may be set to be similar to the thickness of the recess-bottom-surface corresponding section 7A.

The opening defining section 70 of the inner shaping member 7 corresponds to the opening defining section 60 of the outer shaping member 6. In other words, the opening defining section 70 of the inner shaping member 7 is always arranged in opposition to the opening defining section 60 of the outer shaping member 6. As illustrated in FIGS. 3 and 4, the present embodiment, the opening defining section 70 (each linear member 71, 72) of the inner shaping member 7 is in one-to-one correspondence with the opening defining section 60 (each linear member 61, 62) of the outer shaping member 6. It should be noted that the correspondence between the two is not limited to the aforementioned one-to-one correspondence, and the inner shaping member 7 may have an opening defining section 70 (linear members 71, 72) not corresponding to the opening defining section 60 (linear members 61, 62) of the outer shaping member 6.

As illustrated in FIGS. 3 and 4, in the present embodiment, the plurality of openings 65 in the outer shaping member 6 are in one-to-one correspondence with the plurality of openings 75 in the inner shaping member 7. In other words, in a planar view of the collecting/stacking recess 2, one opening 65 overlaps one opening 75. Further, one opening 65 and one opening 75 corresponding therewith (i.e., the openings 65, 75 that overlap one another in a planar view of the collecting/stacking recess 2) are similar to one another in terms of planar-view shape. In the present embodiment, the ratio of similitude of the opening 75 to the corresponding opening 65 is 1 and so, the opening 65 and the opening 75 are congruent in terms of planar-view shape.

Figure 5:
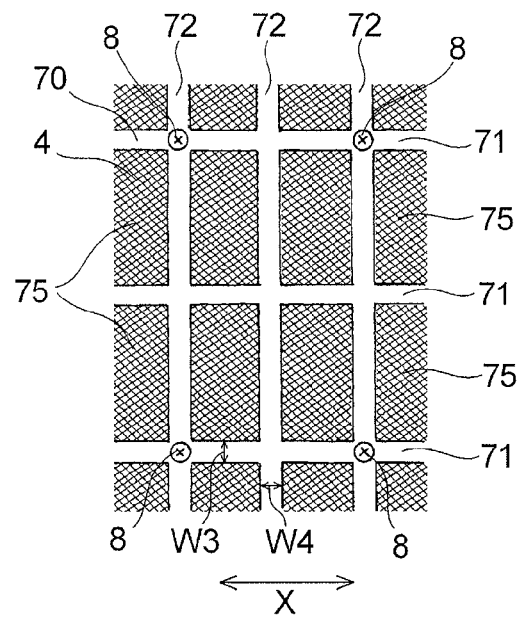
FIG. 5 is a plan view illustrating, in an enlarged state, a portion of a surface of the rotating drum illustrated in FIG. 2 on the opposite side from the bottom surface of the collecting/stacking recess (i.e., a portion of the surface opposing the drum body).

As described above, in the present embodiment, the openings 65 and the openings 75 are in one-to-one correspondence, and the openings 65, 75 in a corresponding relationship are congruent in terms of planar-view shape. Thus, as a matter of course, in the opening defining sections 60, 70 that partition and form the respective openings 65, 75, the number of width-wise linear members 61 and width-wise linear members 71 (the onto bet arranged) is the same, and also, the number of circumference-wise linear members 62 and circumference-wise linear members 72 (the number arranged) is the same, and furthermore, the width (i.e., the length in the direction orthogonal to the linear direction) of the linear members 61, 62 of the outer shaping member 6 is the same as the width of the linear members 71, 72 of the inner shaping member 7 that overlap the respective linear members 61, 62 in a planar view of the collecting/stacking recess 2. In other words, the width W2 (cf. FIG. 4) of each of the circumference-wise linear members 62—which are in a straight line and which constitute the opening defining section 60—is the same as the width W4 (c.f. FIGS. 4 and 5) of each of the circumference-wise linear members 72—which are in a straight line and which constitute the opening defining section 70—that are located right beneath the respective linear members 62 (i.e., on the drum body 3 side) across the porous member 4; and also, the width W1 (not illustrated) of each of the width-wise linear members 61—which are in a straight line and which constitute the opening defining section 60—is the same as the width W3 (cf. FIG. 5) of each of the width-wise linear members 71—which are in a straight line and which constitute the opening defining section 70—that are located right beneath the respective linear members 61 (i.e., on the drum body 3 side) across the porous member 4. The width W1 of each width-wise linear member 61 constituting the opening defining section 60 and the width W2 of each circumference-wise linear member 62 affect the shape of the shaped product (the fiber stack), and are thus set as appropriate depending on the use etc. of the shaped product; the width is preferably 1 mm or greater and more preferably 2 mm or greater, and preferably 10 mm or less and more preferably 8 mm or less. More specifically, the width W1 and the width W2 are each preferably from 1 to 10 mm and more preferably from 2 to 8 mm. The width W3 is in the same range as the width W1 and the width W4 is in the same range as the width W2. The widths W1 and W2 (and the widths W3 and W4) may be the same or different from one another.

It should be noted that, in the present embodiment, the widths (W1 to W4) of the respective linear members 61, 62, 71, 72 do not change and are constant along the thickness direction of the linear members (i.e., the depth direction of the collecting/stacking recess 2), as illustrated for linear members 62, 72 in FIG. 4. However, the widths may be varied along the thickness direction, and, for example, may gradually increase or decrease toward the porous member 4. In such cases, the width (W1 to W4) of each linear member 61, 62, 71, 72 refers to the width of each linear member at the section closest to the porous member 4 (the bottom surface 2A) (the width of the section in contact if the linear member is in contact with the porous member 4).

As described above, in the present embodiment, the air-permeable porous member 4, which forms the bottom surface 2A of the collecting/stacking recess 2, is sandwiched between the outer shaping member 6 and the inner shaping member 7, which are each constituted by a plurality of openings 65, 75 and an opening defining section 60, 70 that partitions and forms the openings 65, 75. Thus, the strength of the bottom section of the collecting/stacking recess 2 is improved and the bottom section is less prone to deform, and the contact between the porous member 4 and the outer shaping member 6—which constitute the inside of the collecting/stacking recess 2—is made tighter, and gaps are less likely to be formed between the bottom surface 2A of the collecting/stacking recess 2 and the opening defining section 60 (the linear members 61, 62) of the outer shaping member 6 located on the bottom surface 2A, compared to cases where the bottom section of the collecting/stacking recess is constituted only by the porous member or cases where the bottom section of the collecting stacking recess is constituted by two layers—i.e., the porous member and a shaping member arranged on the side of one surface of the porous member—as in the later-described rotating drum 80 (cf. FIGS. 11 and 15). Thus, according to the rotating drum 1 of the present embodiment, the above-described faulty transferring of fiber stacks, which is caused by the fiber stacks getting caught in the aforementioned gaps, is less prone to occur, and also, uniform slacking of shaped-product materials inside the collecting/stacking recess 2 is promoted because the vacuum air for carrying the shaped-product materials is rectified easily. Thus, shaped products with good shape and without shape loss can be manufactured efficiently.

Figure 14:
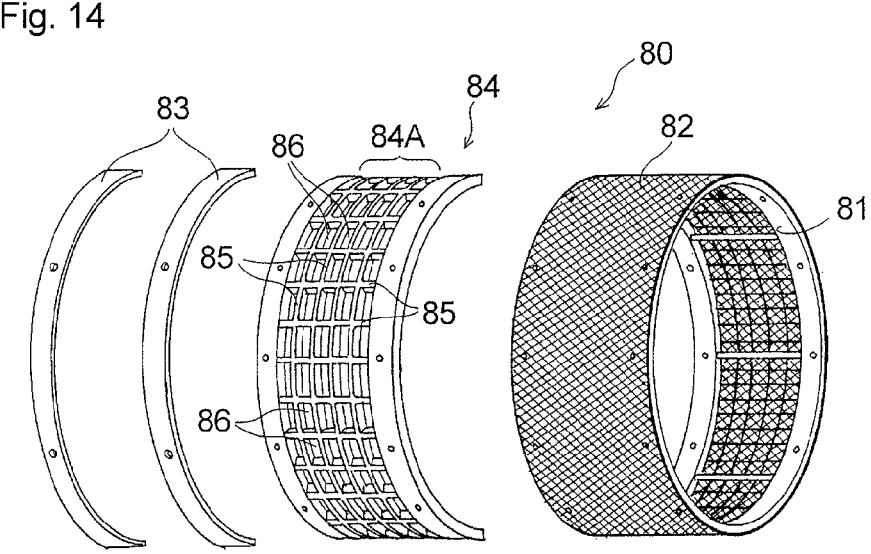
FIG. 14 is a diagram explaining the construction of a rotating drum of a fiber stacking device outside the scope of the present invention.
Figure 15A:
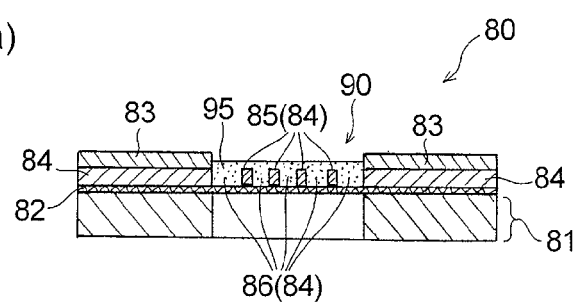
FIG. 15(a) is a cross-sectional view illustrating a state where a shaped-product material has been stacked in the collecting/stacking recess of the rotating drum illustrated in FIG. 14.
Figure 15B:
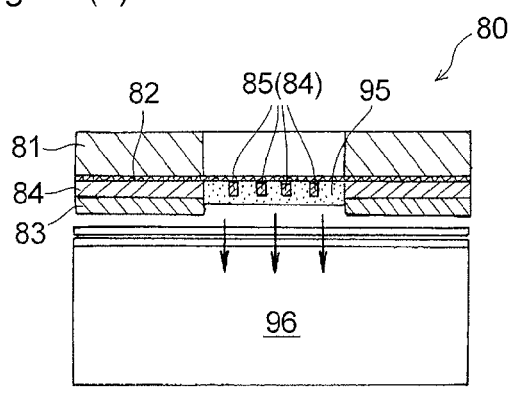
FIG. 15(b) is a diagram explaining a step for releasing a fiber stack from the collecting/stacking recess illustrated in FIG. 15(a) and transferring the fiber stack onto a suction means.
Figure 15C:
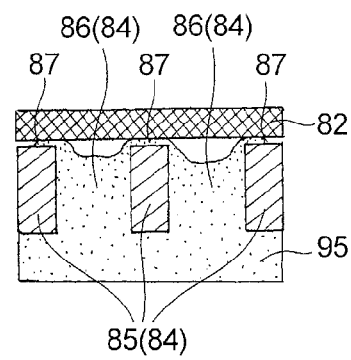
FIG. 15(c) is an enlarged cross-sectional view schematically illustrating a portion of FIG. 15(b) in an enlarged state.

FIGS. 14 and 15 illustrate a rotating drum 80 in which the bottom section of a collecting/stacking recess 90 is constituted by two layers: a porous member 82; and a shaping member 84 arranged on the side of one surface of the porous member 82. The air-impermeable shaping member 84, which inhibits the suction of shaped-product materials from the bottom surface of the collecting/stacking recess 90, is provided on the bottom surface of the recess 90. In general, an "air-impermeable shaping member on the bottom surface of a collecting/stacking recess" is employed with the aim of, for example, partially differentiating the amount of shaped-product materials to be stacked. Such a shaping member, however, may cause faulty transferring of fiber stacks. This is described in further detail in relation to the rotating drum 80. As illustrated in FIG. 15(*a*), the rotating drum 80 has, in its outer peripheral surface, a collecting/stacking recess 90 in which shaped-product materials, such as pulp, are stacked. As illustrated in FIG. 14, the rotating drum 80 includes: a drum body 81; an air-permeable porous member 82 that forms the bottom surface of the collecting/stacking recess 90 and in which a multitude of air-permeation holes are formed; ring members 83 that form the respective inner-side surfaces of the collecting/stacking recess 90 (i.e., the wall surfaces that extend in a direction intersecting with the bottom surface); and a shaping member 84 that is provided between the porous member 82 and the ring members 83 and that partitions the collecting/stacking recess 90 into a plurality of regions along the bottom surface direction. The section 84A, in the shaping member 84, corresponding to the bottom surface of the collecting/stacking recess 90 is formed in a lattice pattern by a plurality of air-impermeable linear members 85 that, in a planar view, are each in a straight line orthogonal to one another. Openings 86 that penetrate the shaping member 84 in thickness direction are formed at positions of the respective cells in the lattice.

If the aforementioned rotating drum 80 is used and shaped-product materials are stacked in the collecting/stacking recess 90 by suction from the bottom surface of the collecting/stacking recess 90 with a suction means (not illustrated) according to an ordinary method, the shaped-product materials are sucked and stacked in the openings 86 with higher priority, because suction from the bottom surface is not performed on the air-impermeable linear members 85. As a result, a fiber stack 95 in which the amount of shaped-product materials stacked is partially different is formed in the collecting/stacking recess 90, as illustrated in FIG. 15(*a*). If this fiber stack 95 in the collecting/stacking recess 90 is sucked by a vacuum conveyor 96 arranged in opposition to the collecting/stacking recess 90 in order to release the fiber stack from the collecting/stacking recess 90 and transfer it onto the vacuum conveyor 96 as illustrated in FIG. 15(*b*), the shaped-product materials constituting the fiber stack 95 may get caught in the gaps 87 formed between the porous member 82 and the linear members 85 as illustrated in FIG. 15(*c*), which may prevent the smooth release of the fiber stack 95 from the recess. Further, because there are a multitude of gaps 87—which may inhibit the smooth release of the fiber stack 95—formed in the collecting/stacking recess 90, faulty transferring of the fiber stack 95 is prone to occur. Furthermore, the gaps 87 disturb the rectification of vacuum air that is generated from inside the rotating drum 80 and that is for carrying the shaped-product materials, and may thus prevent the shaped-product materials from being stacked uniformly and may cause deformations in the shape of the fiber stack (the shaped product). In contrast, the rotating drum 1 of the present embodiment has the aforementioned construction (e.g., the bottom section of the collecting/stacking recess 2 is constituted by three layers: the porous member 4; and shaping members 6, 7 arranged on the side of one surface of the porous member 4 and on the side of the other surface thereof), and is thus superior to the aforementioned rotating drum 80 in terms of for example, transferring properties and shaping properties.

Further, as described above, in the present embodiment, the width of each of the linear members 61, 62 of the outer shaping member 6 is set to be equal to the width of each of the linear members 71, 72 of the inner shaping member 7 that overlap the respective linear members 61, 62 in a planar view of the collecting stacking recess 2 (i.e., W1=W3 and W2=W4). However, excellent results can be obtained, even if the widths of the linear members are made different. More specifically, it the widths W3 and W4 of the linear members 71, 72 or the inner shaping member 7 are greater than the widths W1 and W2 of the linear members 61, 62 of the outer shaping member 6 (W1<W3 and W2<W4), the linear members 71, 72 constituting the opening defining section 70—which are located on the leeward side of the vacuum air flowing from outside the drum toward the inside thereof—will be wider than the linear members 61, 62 constituting the opening defining section 60—which are located on the windward side—and thus, the vacuum air is less prone to enter the gaps between the bottom surface 2A of the collecting/stacking recess 2 and the opening defining section 60 (the linear members 61, 62). Thus, uniform stacking of shaped-product materials inside the collecting/stacking recess 2 is promoted, and faulty fiber-stack transferring and loss of shape are prevented effectively. From the viewpoint of further enhancing the effect of preventing the intrusion of vacuum air into the gaps between the bottom surface 2A and the opening defining section 60, it is preferable that the ratio (W1/W3) between the width W1 of the width-wise linear member 61 of the opening defining section 60 and the width W3 of the corresponding width-wise linear member 71 of the opening defining section 70 is from 0.1 to 1 and more preferably from 0.2 to 0.7. It is also preferable to set the ratio (W2/W4) between the width W2 of the circumference-wise linear member 62 of the opening defining section 60 and the width W4 of the corresponding circumference-wise linear member 72 of the opening defining section 70 within the aforementioned range.

Further, in the present embodiment, because the porous member 4 is sandwiched between the outer shaping member 6 and the inner shaping member 7, it is easier to remove the porous member 4 from the rotating drum 1 compared to cases where the porous member 4 is not sandwiched between the shaping members 6, 7, and replacement can be performed easily in cases where, for example, the porous member 4 gets clogged with shaped-product materials.

The aforementioned inner shaping member 7, the porous member 4, the outer shaping member 6, and the ring members 5 are removably fixed, in this order, to the outer peripheral part of the drum body 3 with, for example, bolts which are not illustrated. In the present embodiment, each of these members to be fixed to the drum body 3 has a length, in the longer direction (the drum's circumferential direction), that substantially half the perimeter or the rotating drum 1, as illustrated in FIG. 3; thus, the rotating drum can be assembled by fixing two of each member to the drum body 3.

In the present embodiment, as illustrated in FIG. 5, the outer shaping member 6 is fixed to the inner shaping member 7 by means of: a plurality of bolt holes (not illustrated) made in the opening defining section 60 in the recess-bottom-surface corresponding section 6A; and bolts 8 inserted in the respective bolt holes. More specifically, as illustrated in FIG. 5, in the recess-bottom-surface corresponding section 7A of the inner shaping member 7 overlapping the recess-bottom-surface corresponding section 6A of the outer shaping member 6 in a planar view of the collecting/stacking recess 2, bolt holes (not illustrated) are made in some of the intersection points between the width-wise linear members 71 and the circumference-wise linear members 72, which constitute the opening defining section 70, so as to penetrate the opening defining section 70 and the porous member 4 in the thickness direction and reach the inside of the opening defining section 60 of the outer shaping member 6 (i.e., the intersection points between the width-wise linear members 61 and the circumference-wise linear members 62, which constitute the opening defining section 60). The outer shaping member 6, the porous member 4, and the inner shaping member 7 are integrated together by means of a plurality of bolts 8 inserted into the respective bolt holes from the surface opposite from the bottom surface 2A of the collecting/stacking recess 2. The bolt holes reach the inside of the opening defining section 60, but do not penetrate the opening defining section 60 in the thickness direction, and thus, the bolts 8 do not protrude from the upper surface of the opening defining section 60 (the surface opposite from the surface opposing the porous member 4). By fixing the recess-bottom-surface corresponding section 6A of the outer shaping member 6 to the recess-bottom-surface corresponding section 7A of the inner shaping member 7 by means of bolts as described above, the contact between the opening defining sections 60, 70 and the porous member 4 is made tighter and gaps are less likely to be formed therebetween, and thus, the aforementioned effect can be achieved more reliably.

Further, in the present embodiment, the air-impermeable ribs 33 of the drum body 3 (cf. FIG. 3) overlap the opening defining sections 60, 70 (the linear members 61, 62, 71, 72) of the outer shaping member 6 and the inner shaping member 7. More specifically, the outer shaping member 6 is fixed to the drum body 3 such that some of the width-wise linear members 61 of the opening defining section 60 that extend in the drum's width direction X overlap the ribs 33 that, in a planar view, are each in a straight line extending in the drum's width direction X. Further, the inner shaping member 7 is also fixed to the drum body 3 such that some of the width-wise linear members 71 of the opening defining section 70 that extend in the drum's width direction X overlap the ribs 33. Because the air-impermeable ribs 33 in the recess-bottom-surface corresponding section 31 of the drum body 3 overlap the linear members 61 (which are a sparingly air-permeable or air-impermeable material) constituting the recess-bottom-surface corresponding section 6A of the outer shaping member 6 and the linear members 71 (which are a sparingly air-permeable or air-impermeable material) constituting the recess-bottom-surface corresponding section 7A of the inner shaping member 7, the of effects brought about by the ribs 33 (i.e., improvement of the strength of the drum body 3 and the bottom section of the collecting/stacking recess 2, and prevention of deformation of the bottom section) can be achieved more reliably while eliminating the problem caused by providing the ribs 33 (i.e., reduction in the force for sucking the shaped-product materials by the vacuum air generated from inside the drum).

In the fiber stacking device 10, a rotation plate is circular in planar view and that rotates by receiving power from a prime mover, such as a motor, is fixed to one end of the rotating drum 1 in the drum's width direction X (the rotation axis direction of the rotating drum 1); the drum body 3, the inner shaping member 7, the porous member 4, the outer shaping member 6, and the ring members 5 rotate integrally about a horizontal axis by the rotation of the rotation plate. On the other hand, a fixed plate that is circular in planar view and that is fixed to other constituent members of the fiber stacking device 10—and thus does not rotate—is fixed to the other end, in the drum's width direction X, of the rotating drum 1. The fixed plate has plates fixed thereto that partition the inside of the rotating drum 1 (the drum body 3) into a plurality or regions in the circumferential direction, and these plates form spaces A, B, and C, which are partitioned from one another, inside the rotating drum 1 (the drum body 3), as illustrated in FIG. 1. In other words, the spaces A to C are partitioned from one another by the plates which are provided from the fixed plate toward the rotation plate. Even when the drum body 3 and the other members fixed to the rotation plate rotate, the plates fixed to the fixed plate do not rotate; thus, the positions of the spaces A, B, and C do not change and are fixed. A known exhaust device (suction means) such as an air-suction fan, which is not illustrated, is connected to the space A; by operating the exhaust device, the inside of the space A can be maintained at negative pressure. While the collecting/stacking recess 2 passes over the space A, which is maintained at negative pressure, the fine air-permeation holes in the porous member 4, which forms the bottom surface 2A of the collecting/stacking recess 2, function as suction holes.

The fiber stacking device 10 will further be described. As illustrated in FIG. 1, the side on one end of the duct 11 covers the outer peripheral surface of the rotating drum 1 located above the space A; and the side of the other end of the duct 11, which is not illustrated, is provided with a shaped-product material introduction device. The shaped-product material introduction device includes, for example, a pulverizer that pulverizes a wood pulp sheet into fibrillated pulp, and that sends the fibrillated pulp (fiber material) into the duct. A water-absorbent polymer introduction unit for introducing water-absorbent polymer particles may be provided in midstream of the duct 11.

The transfer roller 12 has an air-permeable cylindrical outer peripheral part, and the outer peripheral part rotates about a horizontal axis by receiving power from a prime mover, such as a motor. A space D whose inside can be reduced in pressure is formed in the non-rotating section inside the transfer roller 12 (the rotation-axis side). A known exhaust device (not illustrated), such as an air-suction fan, is connected to the space D; by operating the exhaust device, the inside of the space D can be maintained at negative pressure. A multitude of suction holes for communication between the inside and the outside of the roller are formed in the outer peripheral surface of the transfer roller 12. While passing over the space D maintained at negative pressure, the suction holes suck air from outside to the inside, and with this suction force, the fiber stack (shaped product) in the collecting/stacking recess 2 is transferred smoothly from the rotating drum 1 onto the transfer roller 12.

The vacuum box 13 has a box-like shape having upper and lower surfaces, left and right side surfaces, and a rear surface, and has an opening that opens toward the direction of the rotating drum 1. A known exhaust device (not illustrated), such as an air-suction fan, is connected to the vacuum box 13 via, for example, an exhaust pipe which is not illustrated; by operating the exhaust device, the inside of the vacuum box 13 can be maintained at negative pressure. It should be noted that the vacuum box 13 is a device for stably transferring the fiber stack in the collecting/stacking recess 2 without causing the fiber stack to lose its shape; so, in cases where the obtained fiber stack 95 (cf. FIG. 7) is relatively less likely to lose its shape, as in the present embodiment, there is no need to particularly provide the vacuum box, or there is no need to use it even if it is provided. The mesh belt 14 is a member made by endlessly connecting a band-shaped air-permeable belt having meshes, and moves continuously along a predetermined route by being guided by a plurality of free rollers 16 and the transfer roller. The mesh belt 14 is driven by the rotation of the transfer roller 12. As illustrated in FIG. 1, the mesh belt 14 is arranged such that, after being introduced onto the outer peripheral surface of the rotating drum 1 in the vicinity of the downstream end 11*a* of the duct 11, the mesh belt sequentially passes between the vacuum box 13 and the rotating drum 1 and between the transfer roller 12 and the rotating drum 1. The mesh belt 14 is in contact with the outer peripheral surface of the rotating drum 1 while passing the front of the opening in the vacuum box 13, and the mesh belt is separated from the outer peripheral surface of the rotating drum 1 and moves onto the transfer roller 12 in the vicinity of a section where the transfer roller 12 and the rotating drum 1 come nearest to one another.

The mesh belt 14 has fine holes that are smaller than the suction holes of the transfer roller 12; in association with suction from the suction holes of the transfer roller 12, suction is also conducted from the fine holes in the mesh belt 14 that over the suction holes. The windshield plates 15 are provided, in a pair, on opposite sides of a width-wise region where the suction holes are formed in the outer peripheral surface of the transfer roller 12 so as to sandwich this region. The windshield plates 15 prevent or reduce the inflow of air from the sides, and also prevent the fiber stack (shaped product), which has been released from the collecting/stacking recess 2, from losing its shape.

The following describes a method for continuously manufacturing absorbent cores by using the aforementioned fiber stacking device 10—i.e., an embodiment of the absorbent core manufacturing method of the present invention. The manufacturing method of the present embodiment involves a fiber stacking step of sucking and stacking, in the collecting/stacking recess 2 of the rotating drum 1, an absorbent-core material (shaped-product material) supplied on an air stream.

Before executing the fiber stacking step, the space A inside the rotating drum 1, the space D inside the transfer roller 12, and the inside of the vacuum box 13 are reduced to negative pressures by actuating the respective exhaust devices connected thereto. By reducing the inside of the space A to negative pressure, an air stream (vacuum air) for transporting the absorbent-core material onto the outer peripheral surface of the rotating drum 1 is generated inside the duct 11. Also, the rotating drum 1 and the transfer roller 12 are rotated, and the not-illustrated vacuum conveyor arranged below the transfer roller 12 is actuated.

When the fiber material introduction device is actuated and the absorbent-core material is supplied into the duct 11, the absorbent-core material floats on the air stream flowing in the duct 11 and is supplied, in a dispersed airborne state, toward the outer peripheral surface of the rotating drum 1.

Figure 6:
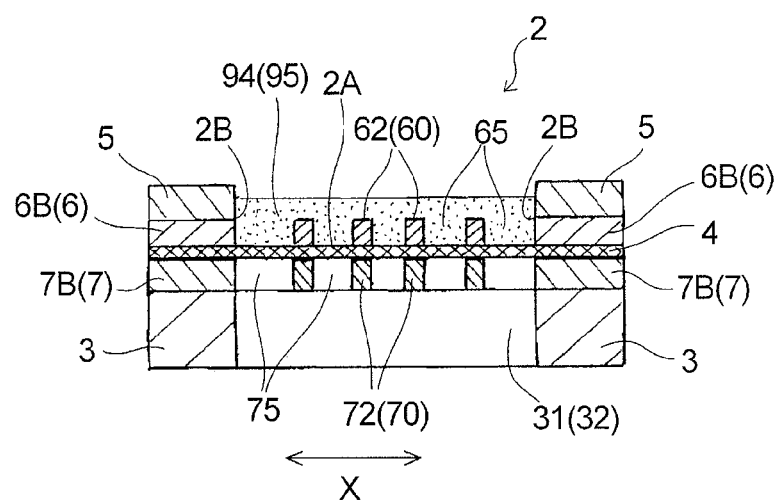
FIG. 6 is a cross-sectional view (corresponding to FIG. 4) illustrating a state where a shaped-product material has bean stacked in the collecting/stacking recess of the rotating drum illustrated in FIG. 2.

While the collecting/stacking recess 2 of the rotating drum 1 is being transported along the section covered by the duct 11, the absorbent-core material 94 is sucked and stacked in the collecting/stacking recess 2, as illustrated in FIG. 6. In the preset embodiment, as illustrated in FIG. 6, the absorbent-core material 94 is stacked not only in the openings 65 of the recess-bottom-surface corresponding section 6A of the outer shaping member 6, where suction from the bottom surface 2A is conducted, but also on the opening defining section 60 (the linear members 61, 62) where suction from the bottom surface 2A is act conducted. On the upstream side of the duct 11, the absorbent-core material is stacked only in the openings 65, but after the height of the stacked absorbent-core material reaches the thickness of the opening defining section 60 (the linear members 61, 62), the absorbent-core material starts getting stacked also on the opening defining section 60 (the linear members 61, 62) in accordance with the intertwining among pieces of the absorbent-core material and the flow of air inside the duct 11 transporting the absorbent-core material. On the downstream side of the duct 11, the collecting/stacking recess 2 is completely covered with the absorbent-core material.

After the absorbent-core material 94 is stacked in the collecting/stacking recess 2 and a fiber stack 95 is obtained, the rotating drum 1 is further rotated. When the fiber stack 95 in the collecting/stacking recess 2 reaches a position in opposition to the vacuum box 13 the fiber stack 95 is sucked onto the mesh belt 14 by suction from the vacuum box 13, and is transported, in this state, to a section where the transfer roller 12 and the rotating drum 1 crane nearest to one another, or to the vicinity thereof. Then, the fiber stack 95, which is sucked on the mesh belt 14, is released from the collecting/stacking, recess 2 by suction from the transfer roller 12 side, and is transferred onto the transfer roller 12 together with the mesh belt 14. By the effects brought about by the specific features of the rotating drum 1 as described above, releasing of the fiber stack 95 from the collecting/stacking recess 2 and transferring of the fiber stack 95 onto the transfer roller 12 occur smoothly without any problems.

Figure 7A:
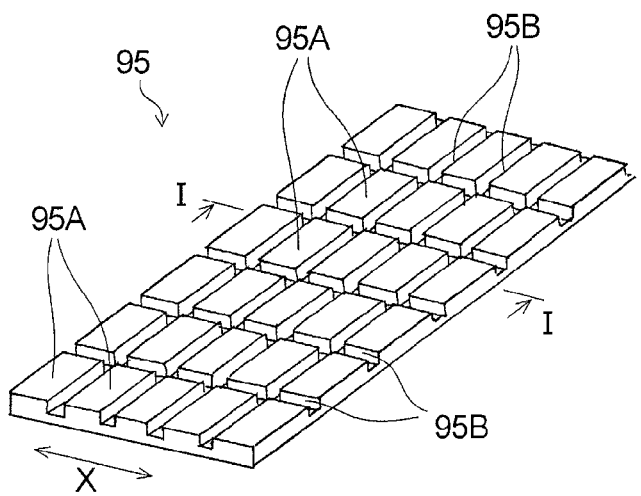
FIG. 7(a) is a perspective view illustrating a fiber stack released from the collecting/stacking recess illustrated in FIG. 6.
Figure 7B:
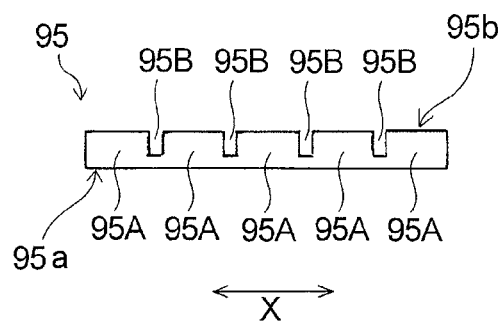
FIG. 7(b) is a cross-sectional view taken along line I-I of FIG. 7(a).

FIG. 7 illustrates a portion of a fiber stack 95 immediately alter being released from the collecting/stacking recess 2. As illustrated in FIG. 7, in the fiber stack 95, sections corresponding to the openings 65 of the recess-bottom-surface corresponding section 6A of the outer shaping member 6 constitute thick sections (high basis-weight sections) 95A in which the amount of absorbent-core material stacked is relatively large, and sections corresponding to the opening defining section 60 (the linear members 61, 62) of the recess-bottom-surface corresponding section 6A constitute thin sections (low basis-weight sections) 95B in which the amount of absorbent-core material stacked is relatively small. Further, one surface 95*a* of the fiber stack 95 is substantially flat, while the other surface 95*b* has a projecting-and-recessed surface with large undulations. The projecting-and-recessed surface 95*b* has a plurality of recesses (grooves; thin sections 95B) that, in planar view, are in continuous straight lines extending in the drum's width direction X and the direction orthogonal thereto (the direction corresponding to the drums circumferential direction), the recesses being arranged in a lattice pattern. The protrusions (thick sections 95A) that have a rectangular shape in planar view are arranged an the respective cells of the lattice.

The fiber stack 95 transferred onto the transfer roller 12 is transported while being sucked from the transfer roller 12 side, and is then passed on to a core-wrap sheet 96 that is made, for example, of tissue paper or a liquid-permeable nonwoven fabric and that has been introduced onto the not-illustrated vacuum conveyor arranged below the transfer roller 12. Then, both side sections of the core-wrap sheet 96 that extend along the transporting direction are folded back, and both the upper and lower surfaces of the fiber stack 95 are covered with the core-wrap sheet 96. Then, if necessary, the fiber stack 95, which is now covered with the core-wrap sheet 96, is compressed in the thickness direction by a compression means (not illustrated) such as a press roller, and is then cut into a predetermined size with a cutter, to thereby obtain an absorbent core which consists of the shaped product covered with the core-wrap sheet 96. It should be noted that in cases where the fiber stack 95 is compressed in the thickness direction, the thick sections (high basis-weight sections) 95A constitute high density sections having a relatively high density, and the thin sections (low basis-weight sections) 95B constitute low density sections having at relatively low density.

The absorbent core of the present invention is suitable as a constituent member of an absorbent article, such as a disposable diaper or a sanitary napkin. An example of an absorbent article employing the absorbent core of the present invention is an article including the aforementioned absorbent core and a sheet material to which the absorbent core is fixed. The sheet material may be arranged only on the side of one surface (the skin-opposing surface or the skin-non-facing surface) of the absorbent core, or may be arranged on both surfaces of the absorbent core. In the latter case, a liquid-permeable topsheet may be used as the sheet material arranged on the skin-facing surface side of the absorbent core, and a liquid-impermeable or water-repellent backsheet may be used as the sheet material arranged on the skin-non-facing surface side of the absorbent core. It should be noted that the skin-facing surface is the surface of the absorbent article, or a constituent member thereof (e.g. the absorbent core), that faces toward the side of the wearer's skin when the absorbent article is worn; the skin-non-facing surface is the surface of the absorbent article, or a constituent member thereof, that faces the opposite side (the clothing side) from the skin side when the absorbent article is worn.

A method for manufacturing an absorbent article including the absorbent core of the present invention and a sheet material to which the absorbent core is fixed involves a step of fixing, onto the sheet material (e.g., topsheet, backsheet, etc.), the absorbent core obtained by executing the aforementioned manufacturing method. The "fixing of the absorbent core to the sheet material" may be perforated by known fixing means, such as a hot-melt adhesive, thermal fusion bonding, or the like. Further, the "fixing of the absorbent core to the sheet material" encompasses sandwiching the absorbent core between at least two sheet materials, without directly joining the absorbent core to the sheet material(s).

The following describes other embodiments of the present invention. The following description on the other embodiments will focus mainly on constituent parts that are different from the foregoing embodiment, and similar constituent parts will be accompanied by the same reference symbols and explanation thereof will be omitted. The explanation given for the foregoing embodiment applies as appropriate to constituent parts that are not particularly explained below.

Figure 8:
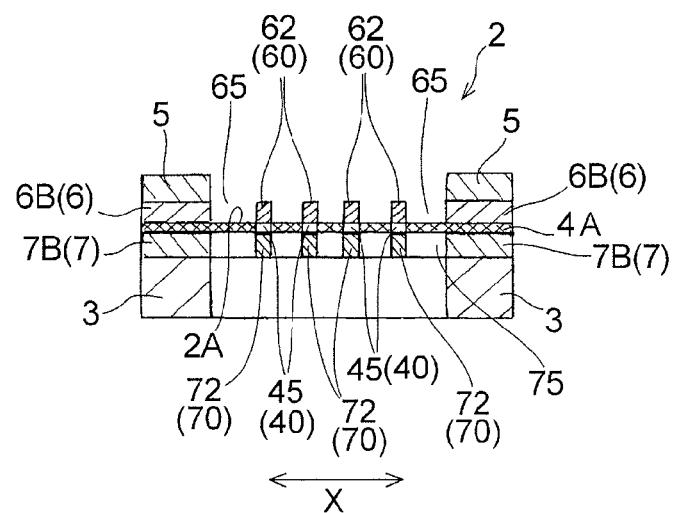
FIG. 8 is a cross-sectional view (corresponding to FIG. 4) illustrating a cross section of the outer peripheral surface, and its vicinity, of another embodiment of a rotating drum according to the present invention, taken along the width direction of the drum.

FIGS. 8 and 9 illustrate another embodiment of the rotating drum according to the present invention. The porous member 4A in the rotating drum of this other embodiment includes an air-impermeable section 45 in a section 40 corresponding to the opening defining section 60 (linear members 61, 62) of the outer shaping member 6 and/or the opening defining section 70 (linear members 71, 72) of the inner shaping member 7 (i.e., the section overlapping the opening defining section 60 and/or the opening defining section 70 in a planar view of the collecting/stacking recess 2; referred to hereinafter also as "opening-defining-section corresponding section 40"). More specifically, as regards the outer shaping member 6 and the inner shaping member 7 which are arranged so as to oppose one another across the porous member 4A, the plurality of openings 65 in the outer shaping member 6 are in one-to-one correspondence with the plurality of openings 75 in the inner shaping member 7, as described above; thus, the opening-defining-section corresponding section 40 of the porous member 4A is the section sandwiched between the opening defining section 60 (linear members 61, 62) of the outer shaping member 6 and the opening defining section 70 (linear members 71, 72) of the inner shaping member 7, as illustrated in FIG. 8, and this section constitutes the air-impermeable section 45.

The air-impermeable section 45 does not have air-permeation holes (holes that penetrate the porous member 4A in the thickness direction) which are formed in other sections the porous member 4A, and is thus air-impermeable. Here, "air impermeability" of the air-impermeable section 45 has the same meaning as the air impermeability of the opening defining sections 60, 70 described above, and means that there is substantially no air permeability. Thus, the air-impermeable section 45 substantially does not allow the passage of vacuum air which flows from the outside of the drum toward the inside thereof at the time of stacking the shaped-product material, and thus functions as a non-suction section where suction from the bottom surface 2A of the collecting/stacking recess 2 is not performed.

FIG. 9 illustrates concrete examples of the air-impermeable section 45. In the embodiment illustrated in FIG. 9(*a*), the entire area of the opening-defining-section corresponding section 40 of the porous member 4A constitutes the air-impermeable section 45, and sections, in the porous member 44, other than the opening-defining-section corresponding section 40 have air-permeation holes and do not constitute air-impermeable sections. In other words, in the embodiment illustrated in FIG. 9(*a*), the air-impermeable section 45 consists of: a plurality of width-wise air-impermeable sections 45A that, in planar view, are in continuous straight lines and that are in one-to-one correspondence with the plurality of width-wise linear members 61 constituting the opening defining section 60 and the plurality of width-wise linear members 71 constituting the opening defining section 70; and a plurality of circumference-wise air-impermeable sections 458 that, in planar view, are in continuous straight lines and that are in one-to-one correspondence with the plurality of circumference-wise linear members 62 (four in this embodiment) constituting the opening defining section 60 and the plurality of circumference-wise linear members 72 (four in this embodiment) constituting the opening defining section 70. The opening defining sections 60, 70 and the air-impermeable section 45 have the same shape in a planar view of the collecting/stacking recess 2, and all have a lattice shape in planar view. From the viewpoint of fiber-stack releasability, the width of the width-wise air-impermeable section 45A of the opening-defining-section corresponding section 40 is preferably the some or greater than the width of the width-wise linear member 61 and width-wise linear member 71. From the same viewpoint, the width of the circumference-wise air-impermeable section 45B of the opening-defining-section corresponding section 40 is preferably the same or greater than the width of the circumference-wise linear member 62 and circumference-wise linear member 72.

Figure 9A:
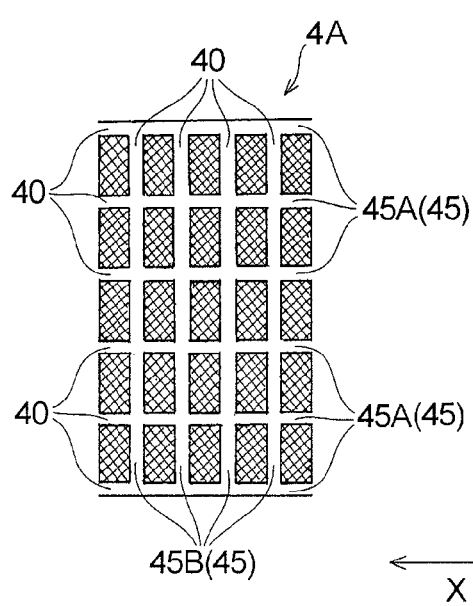
FIGS. 9(a) and 9(b) are plan views illustrating examples of air-impermeable sections in the rotating drum illustrated in FIG. 8.

The air-impermeable section 45 (45A, 45B) illustrated in FIG. 9(a) can be formed by joining a separate air-impermeable member—such as an air-impermeable member made of e.g. metal, resin, or silicone—to a section where the multitude of fine holes (air-permeation holes) are formed in the porous member 4A. Alternatively, the air-impermeable section 45 (45A, 45B) illustrated in FIG. 9(a) may be formed of a section in which air-permeation holes are not formed in the porous member. Specifically, for example, in cases of using, as the porous member 4A, a member in which a multitude of fine holes are formed by etching or punching in an air-impermeable plate made of metal or resin, the air-impermeable section 45 (45A, 45B) illustrated in FIG. 9(a) can be formed by intentionally not forming the fine holes in a predetermined section of the plate.

Alternatively, the air-impermeable section 45 may be formed by joining the porous member 4A (the opening-defining-section corresponding section 40) with the shaping members 6, 7 (the opening defining sections 60, 70 (the linear members 61, 62, 71, 72)). Examples of this joining method include: welding (melt-uniting) in which sections to be joined in the porous member 4A and the shaping members 6, 7 are molten by heat, and the molten sections are directly fused together, and a method in which the porous member 4A is joined with the shaping members 6, 7 by means of an adhesive. The air-permeation holes initially formed in the porous member 4A are closed by welding or with the adhesive, and thus, the section joined to the shaping members 6, 7 by welding or with the adhesive becomes the air-impermeable section 45.

Figure 9B:
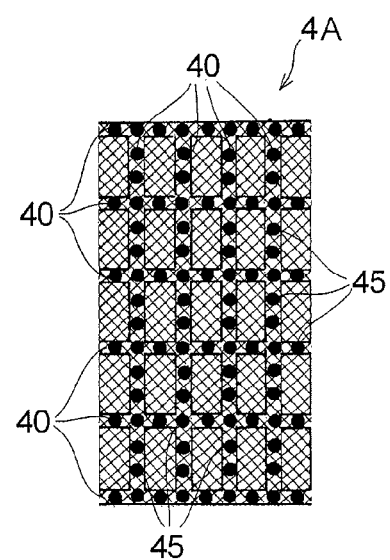

FIG. 9(b) illustrates an example of air-impermeable sections 45 consisting of sections where the porous member 4A is joined to the shaping members 6, 7 by welding or with an adhesive. In the embodiment illustrated in FIG. 9(b), a plurality of air-impermeable sections 45 which are circular in planar a plurality of sections where the porous member 4A is joined to the shaping members 6, 7 by welding or with an adhesive—are formed at predetermined intervals in the opening-defining-section corresponding section 40, which has a lattice shape in planar view, a the porous member 4A; the air-impermeable sections 45 are formed non-consecutively in both the drum's width direction X and the drum's circumferential direction which is orthogonal thereto. A section corresponding to the interval between two adjacent air-impermeable sections 45, 45 has air-permeation holes (air-permeation holes initially formed in the porous member 4A) formed therein, and thus has air permeability.

As described above, the entire area of the opening-defining-section corresponding section 40 of the porous member 4A (i.e., the section overlapping the opening defining sections 60, 70 in a planar view of the collecting/stacking recess 2) may constitute the air-impermeable section 45 as illustrated in FIG. 9(a), or alternatively, only portions (the sections where the porous member 4A is joined to the shaping members 6, 7 by welding or with an adhesive) of the opening-defining-section corresponding section 40 may constitute air-impermeable sections 45 as illustrated in FIG. 9(b), and the opening-defining-section corresponding section 40, as a whole, may have "low air permeability" that is lower than the air permeability of sections, in the porous member 4A, other than the opening-defining-section corresponding section 40.

Even with the other embodiments illustrated in FIGS. 8 and 9, the same effects as those of the foregoing embodiment can be achieved. Particularly, in the other embodiments illustrated in FIGS. 8 and 9, one or more air-impermeable sections 45 are formed in the opening-defining-section corresponding section 40 of the porous member 4A; thus, problems—e.g., the shaped-product materials (absorbent-core materials), such as pulp, getting caught between the porous member 4A and the opening defining section 60 of the outer shaping member 6—are even less likely to occur, and uniform stacking of shaped-product materials inside the collecting/stacking recess 2 is further promoted because the vacuum air for carrying the shaped-product materials is rectified more easily. Thus, shaped products (absorbent cores) with good shape and without shape loss can be manufactured efficiently.

Figure 10:
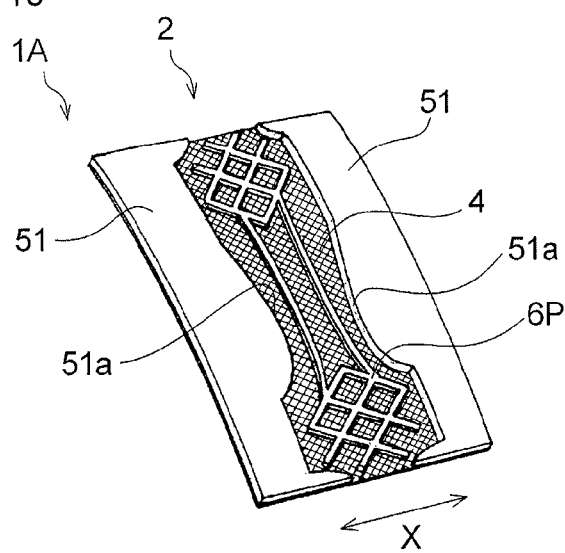
FIG. 10 is a perspective view of a portion of a main part of yet another embodiment of a rotating drum according to the present invention.
Figure 11:
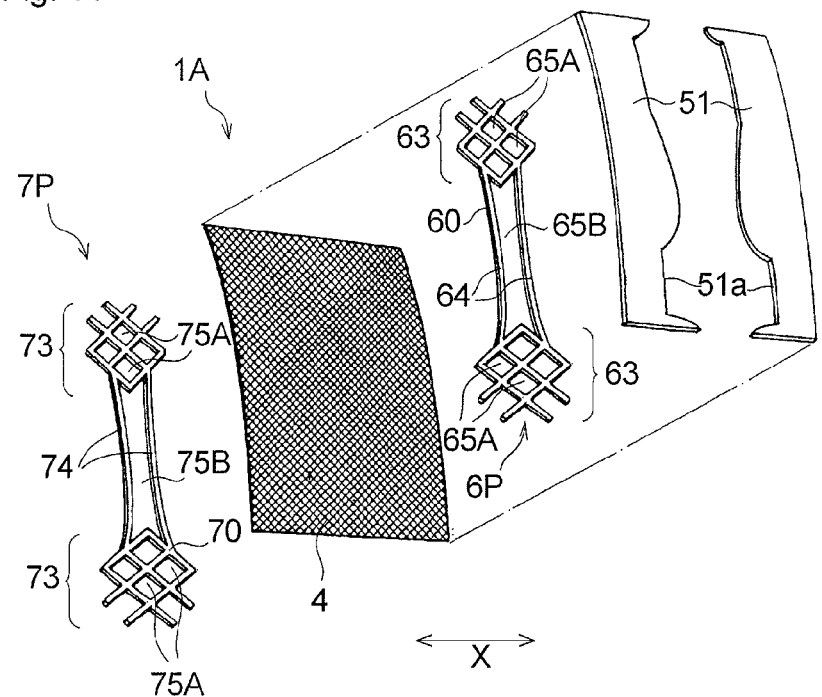
FIG. 11 is a diagram explaining the construction of the main part of the rotating drum illustrated in FIG. 10.
Figure 12:
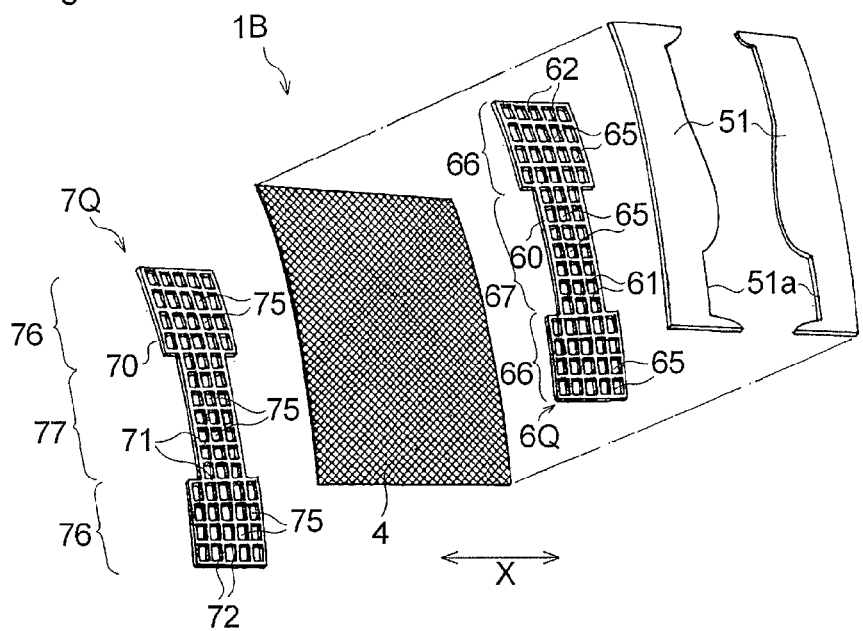
FIG. 12 is diagram, corresponding to FIG. 11, of a main part of yet another embodiment of a rotating drum according to the present invention.
Figure 13:
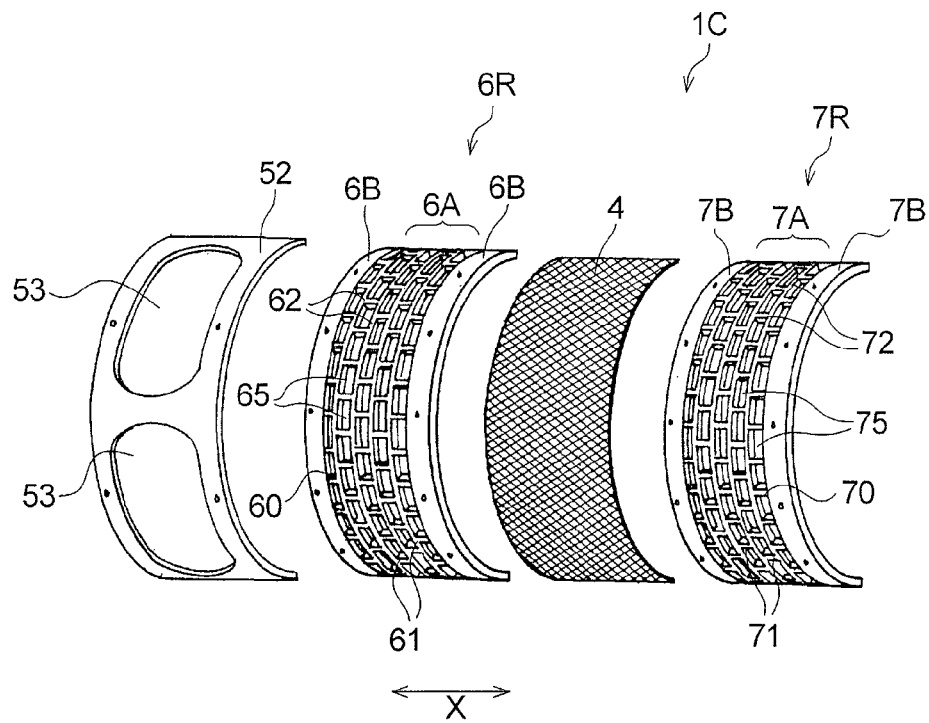
FIG. 13 is a diagram explaining the construction of a main part of yet another embodiment of a rotating drum according to the present invention.

FIGS. 10 to 13 illustrate main parts of rotating drums 1A, 1B and 1C according to further embodiments of the rotating drum of the present invention. Each of the rotating drums 1A, 1B, and 1C is constructed similarly to the foregoing embodiment, except that the shapes of the outer shaping member, the inner shaping member, and the ring members are different. Absorbent cores (shaped products) obtained by using the rotating drum 1A (cf. FIGS. 10 and 11) and absorbent cores (shaped products) obtained by using the rotating drum 1B (cf. FIG. 12) are particularly suitable as absorbent cores for disposable diapers, and absorbent cores (shaped products) obtained by using the rotating drum 1C are particularly suitable as absorbent cores for sanitary napkins. It should be noted that FIGS. 10 to 13 illustrate only a portion, in the circumferential direction, of the rotating drum (FIGS. 10 to 12 illustrate a portion amounting to one unit of an absorbent core, and FIG. 13 illustrates a portion amounting to two units of absorbent cores), and each of the rotating drums 1A, 1B, and 1C is constructed by continuously arranging, in the drum's circumferential direction, a plurality of the aforementioned portions amounting to one or two units of absorbent cores as illustrated in these figures.

As illustrated in FIGS. 10 and 11, in the outer shaping member 6P and the inner shaping member 7P of the rotating drum 1A, the entire shaping members each constitute a recess-bottom-surface corresponding section overlapping the bottom surface 2A (of FIG. 4) of the collecting/stacking recess 2 in a planar view thereof. As illustrated in FIG. 11, the outer shaping member 6P is constituted by: a plurality of openings 65A, 65B that penetrate the outer shaping member 6P (recess-bottom-surface corresponding section) in the thickness direction; and an opening defining section 60 that partitions and forms the openings 65A, 65B. The opening defining section 60 of the outer shaping member 6P consists of: lattice sections 63, 63 that are located at the respective ends, in the drum's circumferential direction, of a portion of the opening defining section 60 amounting to a single absorbent-core unit, and that are each formed in a lattice pattern, in planar view, by a plurality of intersecting linear members which are each in a straight line in planar view; and a pair of non-straight-line linear members 64, 64 that are sandwiched between the lattice sections 63, 63 and that extend in the drum's circumferential direction. The openings 65A are located at the respective lattice cells of each lattice section 63, and each have a square shape in planar view, wherein the diagonal line (not illustrated) of each square shape coincides with the drum's circumferential direction. The opening defining section 60 also includes linear members that look like an extension of the lattice sections 63, 63 in the opposite direction from the opening 65B, and that do not form openings surrounded by the linear members. The opening 65B is located between the pair of linear members 64, 64, and is continuous across the entire length between the lattice sections 63, 63. Each of the linear members 64, 64 is curved such that the central section thereof in the drum's circumferential direction is located more inward, in the drum's width direction X, than the end sections of each linear member 64. As illustrated in FIG. 10, openings in which the shaped-product materials (absorbent-core materials) can be stacked are formed between the outer shaping member 6P and a pair of ring members 51, 51 surrounding it. The opening 65B is located between the pair of linear members 64, 64, and is continuous across the entire length between the lattice sections 63, 63. Each or the linear members 64, 64 is curved such that the central section thereof in the drum's circumferential direction is located more inward, in the drum's width direction X, than the end sections thereof.

The inner shaping member 7P of the rotating drum 1A has the same shape as the outer shaping member 6P, and the dimensions of the parts/members are also the same. As illustrated in FIG. 11, the inner shaping member 7P is constituted by: a plurality of openings 75A, 75B that penetrate the inner shaping member 7P (recess-bottom-surface corresponding section) in the thickness direction; and an opening defining section 70 that partitions and forms the openings 75A, 75B. The opening defining section 70 consists of lattice sections 73, 73 each formed in a lattice pattern, in planar view, by a plurality of intersecting linear members which are each in a straight line in planar view, and a pair of non-straight-line linear members 74, 74 that extend in the drum's circumferential direction and that are sandwiched between the lattice sections 73, 73. The opening defining section 70 (the lattice sections 73 and the linear members 74) of the inner shaping member 7P is in one-to-one correspondence with the opening defining section 60 (the lattice sections 63 and the linear members 64) of the outer shaping member 6P.

As illustrated in FIGS. 10 and 11, in each ring member 51 of the rotating drum 1A, the inner edge 51*a* extending in the drum's circumferential direction includes a curved line, and has a curved section that protrudes inward in the drum's width direction X. The curved section of the inner edge 51*a* of each ring member 51 is located on the outside in the drum's width direction X, of each of the linear members 64, 64. The inner edges 51*a* of the respective ring members 51 are sections that determine the planar-view shape of the length-wise, side edges (in the drum's circumferential direction) of the absorbent core (shaped product) formed in the collecting/stacking recess 2.

The rotating dram 1B illustrated in FIG. 12 is constructed similarly to the rotating drum 1A, except for the outer shaping member 6Q and the inner shaping member 7Q. The outer shaping member 6Q of the rotating drum 1B is constituted by: a plurality openings 65 that penetrate the outer shaping member 6Q (recess-bottom-surface corresponding section) in the thickness direction; and an opening defining section 60 that partitions and forms the openings 65. The entire opening defining section 60 of the outer shaping member 6Q is formed in a lattice pattern, in planar view, by a plurality of intersecting linear members 61, 62 which are each in a straight line in planar view, and the opening defining section 60 includes wide sections 66 whose length in the drum's width direction X is relatively long, and a narrow section 67 whose length is relatively short. The wide sections 66 are located at the respective ends, in the drum's circumferential direction, of a portion of the opening defining section 60 amounting to a single absorbent-core unit. The narrow section 67 is sandwiched between the wide sections 66, 66.

The inner shaping member 7Q of the rotating drum 1B has the same shape as the outer shaping member 6Q, and the dimensions of the parts/members are also the same. As illustrated in FIG. 12, the inner shaping member 7Q is constituted by: a plurality of openings 75 that penetrate the inner shaping member 7Q (recess-bottom-surface corresponding section) in the thickness direction; and an opening defining section 70 that partitions and forms the openings 75. The entire opening defining section 70 is formed in a lattice pattern, in planar view, by a plurality of intersecting linear members 71, 72 which are each in a straight line in planar view, and the opening defining section includes wide sections 76 whose length in the drum's width direction X is relatively long, and a narrow section 77 whose length is relatively short. The wide sections 76 are located at the respective ends, in the drum's circumferential direction, of a portion of the opening defining section 70 amounting to a single absorbent-core unit. The narrow section 77 is sandwiched between the wide sections 76, 76. The opening defining section 70 (the wide sections 76 and the narrow section 77) of the inner shaping member 7Q is in one-to-one correspondence with the opening defining section 60 (the wide sections 66 and the narrow section 67) of the outer shaping member 6Q.

The rotating drum 1C illustrated in FIG. 13 is constructed similarly in the rotating drum 1 illustrated in FIG. 3, except for the ring member 52, the outer shaping member 6R, and the inner shaping member 7R. The ring member 52 of the rotating drum 1C has, in the central section thereof in the drum's width direction X, a plurality of (two) windows 53 thrilled at predetermined intervals in the drum's circumferential direction, each window 53 being oval in planar view and corresponding to a single unit or an absorbent core. The space between the two adjacent windows 53, 53 constitutes a non-fiber-stacking section where no absorbent-core material (shaped-product material) is stacked.

The outer shaping member 6R or the rotating drum 1C is constructed similarly to the outer shaping member 6 of the rotating drum 1 illustrated in FIG. 3, except for the pattern according to which the openings 65 (linear members 61, 62) are arranged. As illustrated in FIG. 13, the plurality of openings 65 in the outer shaping member 6R (recess-bottom-surface corresponding section 6A) are arranged in a staggered pattern. Here, a "staggered pattern" is an arrangement wherein: a plurality of rows, each including a plural it of openings 65 arranged at regular intervals in the drum's circumferential direction, are arranged in the drum's width direction X, which is orthogonal to the drum's circumferential direction; and, in the drum's width direction X, the openings 65 are misaligned (preferably, misaligned by half a pitch) from one another between two adjacent rows. It should be noted that "arranged in a staggered pattern" in the present invention not only encompasses an embodiment in which the openings 65 are arranged perfectly according to the aforementioned explanation, but also encompasses cases where slight unintentional misalignments in arrangement, such as inevitable misalignments during manufacture, have occurred.

The inner shaping member 7R of the rotating drum 1C has the same shape as the outer shaping member 6R, and the dimensions of the parts/members are also the same. As illustrated in FIG. 13, the inner shaping member 7R is constituted by: a plurality of openings 75 that penetrate the recess-bottom-surface corresponding section 7A of the inner shaping member 7R in the thickness direction; and an opening defining section 70 that partitions and forms the openings 75. The openings 75 are arranged in a staggered pattern, and the opening defining section 70 is constituted by including a plurality of intersecting linear members 71, 72 which are each in a straight line in planar view. The opening defining section 70 (the linear members 71, 72) of the inner shaping member 7R is in one-to-one correspondence with the opening defining section 60 (the linear members 61, 62) of the outer shaping member 6R.

The present invention is not limited to the foregoing embodiments and can be modified as appropriate. For example, in the foregoing embodiment, the collecting/stacking recess 2 was formed continuously in the outer peripheral surface of the rotating drum 1 along the entire length in the circumferential direction, but the recess may be formed intermittently in the circumferential direction. In this case, the outermost surface between two collecting/stacking recesses 2, 2 adjacent to one another in the circumferential direction may be formed of an air-impermeable ring member 5, so that shaped-product materials will not get stacked between the recesses 2, 2. Further, in the foregoing embodiment, the members 7, 4, 6, and 5 fixed to the drum body 3 each had a length that is substantially half the perimeter of the rotating drum 1, and two of each member were combined to form the drum. However, each of the members may be made of a single annular member, or alternatively, three or more of each member may be combined. Moreover, the ring members 5 do not have to be arranged outside the outer shaping member 6. Further, the term "linear" in the linear members 61, 62, 64, 71, 72, 74 constituting the opening defining sections 60, 70 is not limited to a straight line in a planar view of the collecting/stacking recess 2, as described in the foregoing embodiments, but encompasses curved lines and beat lines.

Further, in the foregoing embodiment, the outer shaping member 6 and the inner shaping member 7 had a single layer structure. However, they may have a multi-layer structure in which a plurality of relatively thin shaping members are laminated. By providing the outer shaping member 6 and the inner shaping member 7 with multi-layer structures, it becomes possible to process the shaping members easily and manufacture shaped products with various shapes, compared to cases where the shaping members have a single layer structure.

Further, in the foregoing embodiment, the bolts 3 for fixing the outer shaping member 6 to the inner shaping member 7 were inserted from the side of the inner shaping member 7 toward the side of the outer shaping member 6 (i.e., from the inside of the drum toward the outside). However, the bolts may be inserted oppositely from the outer shaping member 6 side toward the inner shaping member 7 side (i.e., from the outside of the drum toward the inside).

Further, the foregoing embodiment, the openings 65 were in one-to-one correspondence with the openings 75, and the planar-view shapes of corresponding openings 65, 75 were congruent; thus, the opening defining section 60 of the outer shaping member 6 and the opening defining section 70 of the inner shaping member 7 were congruent in terms of planar-view shape and thus entirely overlapped one another in a planar view of the collecting stacking recess 2. However, the planar-view shapes of the opening defining sections 60, 70 do not have to be the same, and only a portion thereof may overlap one another in a planar view of the collecting/stacking recess 2. For example, the opening defining section 70 of the inner shaping member 7 may be formed in a lattice pattern in planar view as illustrated in FIG. 3, and the opening defining section 60 of the outer shaping member 6 may be constituted only by a plurality of width-wise air-impermeable members that, in planar view, are in straight lines extending in the drum's width direction X, and thus formed in a ladder pattern in planar view.

Further, in the foregoing embodiment, the ring members 5 were attached to the outer peripheral surface of the rotating drum 1. However, the ring members do not have to be used, and protrusions may be formed on the side sections of the outer shaping member 6, and the protrusions may be employed as members achieving the same effect as the ring members. Further, in the foregoing embodiment, the length of each ring member 5 in the drum's width direction was constant, but the length of each ring member 5 in the drum's width direction may be changed along the drum's circumferential direction by, for example, changing the shape of the inner edge or each ring member 5 (i.e., the side edge on the inner end surface side) along the drum's circumferential direction. In this way, the width and shape of the shaped product can be changed along the drum's circumferential direction. Parts/members in any one of the foregoing embodiments can all be mutually employed, as appropriate, in other embodiments.

In relation to the for going embodiments of the present invention, the following additional features (for the fiber stacking device, the absorbent core manufacturing method, and the absorbent article manufacturing method) are disclosed.

<1> A fiber stacking device comprising a rotating drum that has a collecting/stacking recess in an outer peripheral surface thereof, wherein the rotating drum forms a shaped product by stacking a shaped-product material by sucking the material with a bottom surface of the collecting/stacking recess, wherein:

the rotating drum includes a drum body, and an air-permeable porous member that forms the bottom surface of the collecting/stacking recess;

the porous member is sandwiched between an outer shaping member arranged so as to oppose the bottom surface of the collecting/stacking recess, and an inner shaping member arranged between the porous member and the drum body; both the shaping members are arranged so as to overlap the porous member;

each of the shaping members has a recess-bottom-surface corresponding section that overlaps the bottom surface of the collecting/stacking recess in a planar view of the collecting/stacking recess; each the recess-bottom-surface corresponding section is constituted by a plurality of openings that penetrate the recess-bottom-surface corresponding section in the thickness direction, and an opening defining section that partitions and forms the openings; and the opening defining section of the inner shaping member corresponds to the opening defining section of the outer shaping member.

<2> The fiber stacking device according to the aforementioned item <1>, wherein the opening defining section of the respective shaping members is air-impermeable.

<3> The fiber stacking device according to the aforementioned item <1> or <2>, wherein the porous member includes an air-impermeable section in a section corresponding to the opening defining section of the cuter shaping member and or the inner shaping member.

<4> The fiber stacking device according to the aforementioned item <3>, wherein the air-impermeable section is formed by joining the porous member with the outer shaping member and the inner shaping member.

<5> The fiber stacking device according to the aforementioned item <3> or <4>, wherein the air-impermeable section is formed by: (1) a welding (melt-uniting) method in which sections to be joined in the porous member, the outer shaping member, and the inner shaping member are molten by heat, and the molten sections are directly fused together; or (2) a method in which the porous member is joined with the outer shaping member and the inner shaping member by means of an adhesive.

<6> The fiber stacking device according to any one of the aforementioned items <3> to <5>, wherein either: the entire area of an opening-defining-section corresponding section (a section overlapping the opening defining section of the outer shaping member and the opening defining section or the inner shaping member in a planar view of the collecting/stacking recess) of the porous member constitutes the air-impermeable section; or only a portion (a section where the porous member and both the shaping members are joined by welding or with an adhesive) of the opening-defining-section corresponding section constitutes the air-impermeable section, and the opening-defining-section corresponding section, as a whole, has low air permeability that is lower than the air permeability of sections, in the porous member, other than the opening-defining-section corresponding section.

<7> The fiber stacking device according to any one of the aforementioned items <1> to <6>, wherein the plurality of the openings disposed in the outer shaping member are in one-to-one correspondence with the plurality of the openings disposed in the inner shaping member.

<8> The fiber stacking device according to the aforementioned item <7>, wherein, in a planar view of the collecting/stacking recess, the openings in the outer shaping member and the openings in the inner shaping member overlap one another.

<9> The fiber stacking device according to the aforementioned item <7> or <8>, wherein, in a planar view of the collecting/stacking, recess, wherein, in a planar view of the collecting/stacking recess, the opening disposed in the outer shaping member and the opening disposed in the inner shaping member that overlap one another are congruent to or similar to one another in terms of planar-view shape.

<10> The fiber stacking device according to any one of the aforementioned items <1> to <9>, wherein the opening defining section of the respective shaping members is constituted by linear members extending along the bottom surface of the collecting/stacking recess.

<11> The fiber stacking device according to the aforementioned item <10>, wherein: the opening defining section of each of the outer shaping member and the inner shaping member includes, as the aforementioned linear members, a plurality of width-wise linear members that, in a planar view, are each in a straight line extending in the width direction of the drum, and a plurality of circumference-wise linear members that, in a planar view, are each in a straight line orthogonal to the plurality of width-wise linear members, and each opening defining section is formed in a lattice pattern, in planar view, by the linear members; and the openings in each shaping member are located at the respective cells of the lattice, and each have a rectangular shape in a planar view.

<12> The fiber stacking device according to the aforementioned item <10> or <11>, wherein the width of the linear member (of the opening defining section) of the outer shaping member is the same as the width of the linear member (of the opening defining section) of the inner shaping member located right beneath the aforementioned linear member across the porous member.

<13> The fiber stacking device according to the aforementioned item <10> or <11>, wherein the width of the linear member (of the opening defining section) of the outer shaping member is different from the width of the linear member (of the opening defining section) of the inner shaping member that overlaps the linear member of the outer shaping member in a planar view of the collecting/stacking recess.

<14> The fiber stacking device according to the aforementioned item <13>, wherein the width of the linear member (of the opening defining section) of the inner shaping member is greater than the width of the linear member (of the opening defining section) of the outer shaping member.

<15> The fiber stacking device according to any one of the aforementioned items <10> to <14>, wherein the ratios ($W_1/W_3$ and $W_2/W_4$) between the widths $W_1$ and $W_2$ of the linear members (of the opening defining section) of the outer shaping member and the respectively corresponding widths $W_3$ and $W_4$ of the linear members (of the opening defining section) of the inner shaping member are from 0.1 to 1, or from 0.2 to 0.7.

<16> The fiber stacking device according to any one of the aforementioned items <10> to <15>, wherein the width of each linear member constituting the opening defining section of the outer shaping member is from 1 to 10 mm.

<17> The fiber stacking device according to any one of the aforementioned items <1> to <16>, wherein the outer shaping member is fixed to the inner shaping member by means of: a plurality of bolt holes made in the opening defining section in the recess-bottom-surface corresponding section; and bolts inserted in the respective bolt holes.

<18> The fiber stacking device according to any one of the aforementioned items <1> to <17>, wherein;
the drum body has a recess-bottom-surface corresponding section that overlaps the bottom surface of the collecting/stacking recess in a planar view of the collecting/stacking recess; the recess-bottom-surface corresponding section is constituted by a plurality of through holes that penetrate the recess-bottom-surface corresponding section in the thickness direction, and air-impermeable ribs each located between the two adjacent through holes; and
in a planar view of the collecting/stacking recess, the ribs overlap the opening defining sections of the respective shaping members.

<19> The fiber stacking device according to any one of the aforementioned items <1> to <18>, wherein the bottom surface of the collecting/stacking recess has a flat form.

<20> The fiber stacking device according to any one of the aforementioned items <1> to <19>, wherein:
the drum body is made of a stiff, metal tube, and has, in the central section in the width direction of the drum, a recess-bottom-surface corresponding section that overlaps the bottom surface of the collecting/stacking recess in a planar view thereof; and
the recess-bottom-surface corresponding section is constituted by a plurality of through openings that penetrate the recess-bottom-surface corresponding section in the thickness direction, and air-impermeable ribs each located between two adjacent through openings.

<21> The fiber stacking device according to any one of the aforementioned items <1> to <20>, wherein: the porous member is a metal or resin mesh, or a porous metal plate or resin plate in which a multitude of fine holes are formed in a metal or resin plate by etching or punching; and air-permeation holes having a diameter of from 0.2 to 0.6 mm are formed in the porous member at a pitch of from 0.4 to 1.5 mm.

<22> The fiber stacking device according to any one of the aforementioned items <1> to <21>, wherein: the rotating drum includes ring members that form the respective inner-side surfaces of the collecting/stacking recess; and the ring members are arranged on the respective side sections, in the width direction, of the outer peripheral surface of the rotating drum with the collecting/stacking recess sandwiched therebetween.

<23> The fiber stacking device according to any one of the aforementioned items <1> to <22>, wherein the opening defining section of the inner shaping member is always arranged in opposition to the opening defining section of the outer shaping member, but the inner shaping member has an opening defining section that does not correspond to the opening defining section of the outer shaping member.

<24> The fiber stacking device according to any one of the aforementioned items <1> to <23>, wherein the collecting/stacking recess is either formed continuously in the outer peripheral surface of the rotating drum along the entire length in the circumferential direction, or formed intermittently along the circumferential direction.

<25> The fiber stacking device according to any one of the aforementioned items <1> to <24>, wherein the fiber stacking device includes: a duet that supplies the shaped-product material to the outer peripheral surface of the rotating drum; a transfer roller that is driven to rotate and that is arranged obliquely below the rotating drum; and a vacuum conveyor arranged below the transfer roller.

<26> The fiber stacking device according to the aforementioned item <25>, wherein the fiber stacking device includes: a vacuum box provided between the duct and the transfer roller in the circumferential direction of the rotating drum, and a mesh belt arranged so as to pass between the vacuum box and the rotating drum and between the is transfer roller and the rotating drum.

<27> A method for manufacturing an absorbent core by using fiber stacking device according to any one of the aforementioned items <1> to <24>, the absorbent core manufacturing method comprising:
a fiber stacking step of sucking and stacking, in the collecting/stacking recess of the rotating drum, an absorbent-core material supplied on an air stream.

<28> A method for manufacturing an absorbent core by using the fiber stacking device according to the aforementioned item <25>, the absorbent core manufacturing method including:
a fiber stacking step of sucking and stacking, in the collecting/stacking recess of the rotating drum, an absorbent-core material supplied on an air stream.

<29> A method for manufacturing an absorbent core by using the fiber stacking device according to the aforementioned item <26>, the absorbent core manufacturing method including:
a fiber stacking step of sucking and stacking, in the collecting/stacking recess of the rotating drum, an absorbent-cote material supplied on an air stream.

<30> The absorbent core manufacturing method according to the aforementioned item <28> or <29>, wherein the absorbent-core material is sucked and stacked in the collecting/stacking recess while the collecting/stacking recess of the rotating drum is being transported along a section covered by the duct.

<31> The absorbent core manufacturing method according to the aforementioned item <29>, including the steps of:
obtaining a fiber stack by stacking the absorbent-core material in the collecting/stacking recess; then further rotating the rotating drum; sucking the fiber stack onto the mesh belt at a position in opposition to the vacuum box; transporting the fiber stack in this state to a section where the transfer roller and the rotating drum come nearest to one another, or to the vicinity thereof; releasing the fiber stack from the collecting/stacking recess by suction from the transfer roller side; and transferring the fiber stack onto the transfer roller together with the mesh belt;
then passing the fiber stack, which has been transferred onto the transfer roller, on is to a core-wrap sheet that has been introduced onto the vacuum conveyor arranged below the transfer roller; and
then folding back both side sections of the core-wrap sheet that extend along the transporting direction, and covering the fiber stack with the core-wrap sheet.

<32> The absorbent core manufacturing method according to any one of the aforementioned items <27> to <29>, wherein the absorbent-core material is stacked not only in the openings in the recess-bottom-surface corresponding section of the outer shaping member where suction from the bottom surface of the collecting/stacking recess is performed, but is stacked also on the opening defining section (the linear members) of the outer shaping member where suction from the bottom surface is not performed.

<33> A method for manufacturing an absorbent article that includes an absorbent core and a sheet material to which the absorbent core is fixed, absorbent article manufacturing method comprising:
a step of fixing, onto the sheet material, the absorbent core obtained by executing the manufacturing method according to any one of the aforementioned items <27> to <32>.

The invention claimed is:
1. A fiber stacking device for forming a shaped product, the device comprising:
  a rotating drum that has, in an outer peripheral surface thereof, a collecting/stacking recess for forming the shaped product by stacking a shaped-product material by sucking the material with a bottom surface of the collecting/stacking recess, wherein
  the rotating drum comprises:
  a drum body;
  an inner shaping member;
  an outer shaping member; and
  an air-permeable porous member that forms the bottom surface of the collecting/stacking recess,
  each of the inner and outer shaping members has an opening defining section that partitions and forms a plurality of openings,
  the inner shaping member is disposed on an outer peripheral surface of the drum body,
  the air-permeable porous member is disposed on the inner shaping member,
  the outer shaping member is disposed on the air-permeable porous member, so that i) the air-permeable porous member is sandwiched between the outer shaping member and the inner shaping member ii) the inner and outer shaping members are arranged so as to overlap with the air-permeable porous member, iii) the openings of the inner and outer shaping members overlap with each other via the air-permeable porous member so that the opening defining section of the outer shaping member and the air-permeable porous member define together the collecting/stacking recess in a planar view thereof, an air permeability of the opening defining section of each said shaping member is lower than an air permeability of the air-permeable porous member, the plurality of the openings of the outer shaping member respectively overlap with the plurality of the openings of the inner shaping member, so that in a planar view of the collecting/stacking recess, the opening of the outer shaping member and the opening disposed in the inner shaping member which overlaps with the opening of the outer shaping member have substantially the same shape in terms of planar-view shape.

2. The fiber stacking device according to claim 1, wherein the opening defining section of each said shaping member is air-impermeable.

3. The fiber stacking device according to claim 1, wherein the porous member includes an air-impermeable section in a section corresponding to the opening defining section of the outer shaping member or the inner shaping member.

4. The fiber stacking device according to claim 3, wherein the air-impermeable section is formed by joining the porous member with the outer shaping member and the inner shaping member.

5. The fiber stacking device according to claim 3, wherein the air-impermeable section is formed by: (1) a welding method in which sections to be joined in the porous member, the outer shaping member, and the inner shaping member are molten by heat, and the molten sections are directly fused together; or (2) a method in which the porous member is joined with the outer shaping member and the inner shaping member by means of an adhesive.

6. The fiber stacking device according to claim 3, wherein the porous member includes an opening-defining-section corresponding section in a section corresponding to the opening defining section of the outer shaping member or the inner shaping member, an entire area or a partial area of the opening-defining-section corresponding section constitutes the air-impermeable section, and the opening-defining-section corresponding section, as a whole, has an air permeability, which is lower than the air permeability of sections, in the porous member, other than the opening-defining-section corresponding section.

7. The fiber stacking device according to claim 1, wherein the opening defining section of each of the inner and outer shaping members is constituted by linear members extending along the bottom surface of the collecting/stacking recess.

8. The fiber stacking device according to claim 7, wherein the width of each of the linear members of the outer shaping member is different from the width of each of the linear members of the inner shaping member that overlaps the linear member of the outer shaping member in a planar view of the collecting/stacking recess.

9. The fiber stacking device according to claim 1, wherein a plurality of bolt holes are made in the opening defining section of the inner shaping member, the outer shaping member is fixed to the bolt holes of the inner shaping member by bolts.

10. The fiber stacking device according to claim 1, wherein:

the drum body has a recess-bottom-surface corresponding section that overlaps the bottom surface of the collecting/stacking recess in a planar view of the collecting/stacking recess; the recess-bottom-surface corresponding section is constituted by a plurality of through holes that penetrate the recess-bottom-surface corresponding section in the thickness direction, and air-impermeable ribs each located between the two adjacent through holes; and in a planar view of the collecting/stacking recess, the ribs overlap the opening defining sections of the respective shaping members.

11. The fiber stacking device according to claim 1, wherein the bottom surface of the collecting/stacking recess has a flat form.

12. A fiber stacking device for forming a shaped product, the device comprising:

a rotating drum that has, in an outer peripheral surface thereof, a collecting/stacking recess for forming the shaped product by stacking a shaped-product material by sucking the material with a bottom surface of the collecting/stacking recess, wherein the rotating drum comprises:

a drum body;

an inner shaping member;

an outer shaping member; and an air-permeable porous member that forms the bottom surface of the collecting/stacking recess, each of the inner and outer shaping members has an opening defining section that partitions and forms a plurality of openings, the inner shaping member is disposed on an outer peripheral surface of the drum body, the air-permeable porous member is disposed on the inner shaping member, the outer shaping member is disposed on the air-permeable porous member, so that i) the air-permeable porous member is sandwiched between the outer shaping member and the inner shaping member ii) the inner and outer shaping members are arranged so as to overlap with the air-permeable porous member, iii) the openings of the inner and outer shaping members overlap with each other via the air-permeable porous member so that the opening defining section of the outer shaping member and the air-permeable porous member define together the collecting/stacking recess in a planar view thereof, an air permeability of the opening defining section of each said shaping member is lower than an air permeability of the air-permeable porous member, the inner shaping member and the outer shaping member are disposed so that the opening defining section of the inner shaping member opposes to the opening defining section of the outer shaping member, and each of the opening defining sections of the inner and outer shaping members is constituted by linear members, and a width of each of the linear members of the outer shaping member is equal to a width of each of the linear members of the inner shaping member that overlap the linear members in a planar view, or the widths of the linear members of the inner shaping member are greater than the widths of the linear members of the outer shaping member.

13. A method for manufacturing an absorbent article that includes an absorbent core and a sheet material to which the absorbent core is fixed, the absorbent article manufacturing method comprising:

a step of providing a fiber stacking device comprising:

a rotating drum that has, in an outer peripheral surface thereof, a collecting/stacking recess for forming the shaped product by stacking a shaped-product material by sucking the material with a bottom surface of the collecting/stacking recess, wherein the rotating drum comprises:

a drum body;

an inner shaping member;

an outer shaping member; and an air-permeable porous member that forms the bottom surface of the collecting/stacking recess, each of the inner and outer shaping members has an opening defining section that partitions and forms a plurality of openings, the inner shaping member is disposed on an outer peripheral surface of the drum body, the air-permeable porous member is disposed on the inner shaping member, the outer shaping member is disposed on the air-permeable porous member, so that i) the air-permeable porous member is sandwiched between the outer shaping member and the inner shaping member ii) the inner and outer shaping members are arranged so as to overlap with the air-permeable porous member, iii) the openings of the inner and outer shaping members overlap with each other via the air-permeable porous member so that the opening defining section of the outer shaping member and the air-permeable porous member define together the collecting/stacking recess in a planar view thereof, an air permeability of the opening defining section of each said shaping member is lower than an air permeability of the air-permeable porous member, the plurality of the openings of the outer shaping member respectively overlap with the plurality of the openings of the inner shaping member, so that in a planar view of the collecting/stacking recess, the opening of the outer shaping member and the opening disposed in the inner shaping member which overlaps with the opening of the outer shaping member have substantially the same shape in terms of planar-view shape;

a fiber stacking step of sucking and stacking, in the collecting/stacking recess of the rotating drum, an absorbent-core material supplied in an air stream so as to obtain the absorbent core; and a step of fixing the absorbent core to the sheet material.

* * * * *